US006268514B1

(12) United States Patent
Hamprecht et al.

(10) Patent No.: US 6,268,514 B1
(45) Date of Patent: Jul. 31, 2001

(54) USE OF NITROETHANE DERIVATIVES AS MICROBICIDES AND SPECIFIC NITROETHANE DERIVATIVES

(75) Inventors: Gerhard Hamprecht, Weinheim; John-Bryan Speakman, Bobenheim; Gisela Lorenz, Neustadt; Kurt Eger, Leipzig; Mathias Schmidt, Greffen; Uta Witt, Bad Münstereifel, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/581,420

(22) PCT Filed: Dec. 2, 1998

(86) PCT No.: PCT/EP98/07815

§ 371 Date: Jun. 13, 2000

§ 102(e) Date: Jun. 13, 2000

(87) PCT Pub. No.: WO99/31108

PCT Pub. Date: Jun. 24, 1999

(30) Foreign Application Priority Data

Dec. 13, 1997 (DE) .................................... 197 55 62

(51) Int. Cl.[7] ........................ C07D 493/02; C07D 493/04
(52) U.S. Cl. .................... 549/306; 549/304; 549/311; 549/312
(58) Field of Search .................. 549/306, 311, 549/312, 304

(56) References Cited

PUBLICATIONS

Schmidt et al. "Michael reaction of ascorbic acid, 4th communication [1:] Nitrostyrene as a Michael acceptor toward Vitamin", Pharmazie No. 51, (1996) pp. 11–16.

El–Ablack et al. "Synthesis of Some New Antimicrobal – Pyrazolin–5–Ones of Pharmaceutical Interest", Pakistan Journal of Scientific and Industrial Research (1993) pp. 77–79.

Kaminski et al., "New Aspects of the Possibility of Using 1.3–indandione Derivatives" Przemysl Chemiczny (1977) pp. 23–26.

Primary Examiner—Ba K. Trinh
(74) Attorney, Agent, or Firm—Keil & Weinakuf

(57) ABSTRACT

The use of nitroethane derivatives of the formula I

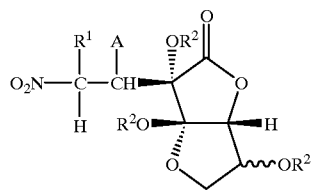

where:

$R^1$ is hydrogen, unsubstituted or substituted $C_1$–$C_6$-alkyl, $C_3$–$C_6$-alkenyl, $C_3$–$C_6$-alkynyl, halogen, cyano or thiocyanato;

$R^2$ is hydrogen, formyl; halogen- or $C_1$–$C_3$-alkoxy-substituted or unsubstituted $C_1$–$C_6$-alkylcarbonyl, $C_2$–$C_6$-alkenylcarbonyl, $C_4$–$C_6$-alkyldienylcarbonyl or $C_2$–$C_6$-alkynylcarbonyl;

A is unsubstituted or substituted phenyl, naphthyl, quinolyl, quinazolyl, quinoxalyl, 1-methylindolyl, 1-methylbenzimidazolyl, 2-methylindazolyl, benzofuranyl, benzothienyl, benzoxazolyl, benzothiazolyl, furyl, thienyl, pyrrolyl, isoxazolyl, isothiazolyl, pyrazolyl, oxazolyl, thiazolyl, imidazolyl, oxadiazolyl, thiadiazolyl, triazolyl, pyridinyl, pyridazinyl, pyrimidinyl, pyrazinyl or triazinyl, pyranyl or thiopyranyl;

as microbicides is described.

16 Claims, No Drawings

USE OF NITROETHANE DERIVATIVES AS MICROBICIDES AND SPECIFIC NITROETHANE DERIVATIVES

This application is a 371 of PCT/EP98/07815 dated Dec. 2, 1998.

The present invention relates to the use of nitroethane derivatives as microbicides, to specific novel nitroethane derivatives and to processes for their preparation.

Some of these nitroethane derivatives, such as, for example, the compound α-L-xylo-3-hexulofuranosonic acid, 2-C-[2-nitro-1-phenylethyl], γ lactone [CA-Reg. No. 175 433-01-09], the corresponding 4-chlorophenyl compound [CA-Reg. No. 175 433-02-0], 2,6-dichlorophenyl compound [CA-Reg. No. 175 433-03-01], 2-methoxyphenyl compound [CA-Reg. No. 175 433-04-02], 3-methoxyphenyl compound [CA-Reg. No. 175 433-05-03], 4-methoxyphenyl compound [CA-Reg. No. 175 433-06-04], 3-hydroxy-4-methoxyphenyl compound [CA-Reg. No. 175 433-07-05], and 4-methylphenyl compound [CA-Reg. No. 175 433-08-06], have already been disclosed. Hitherto, only the virostatic and cytostatic properties of these compounds have been investigated (see Pharmazie 51 (1996), 11–16).

A microbicidal activity of these compounds has hitherto not been disclosed.

We have found that nitroethane derivatives, some of which are known, of the formula I

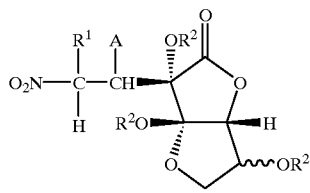

I where:
R[1] is hydrogen, $C_1$–$C_6$-alkyl which may be substituted by halogen, cyano, hydroxycarbonyl, $C_1$–$C_3$-alkoxy, $C_1$–$C_3$-alkylthio, $C_1$–$C_3$-alkoxycarbonyl, or is $C_3$–$C_6$-alkenyl, $C_3$–$C_6$-alkynyl, halogen, cyano or thiocyanato;

R[2] is hydrogen, formyl; halogen- or $C_1$–$C_3$-alkoxy-substituted or unsubstituted $C_1$–$C_6$-alkylcarbonyl, $C_2$–$C_6$-alkenylcarbonyl, $C_4$–$C_6$-alkyldienylcarbonyl or $C_2$–$C_6$-alkynylcarbonyl;

A is phenyl, naphthyl, quinolyl, quinazolyl, quinoxalyl, 1-methylindolyl, 1-methylbenzimidazolyl, 2-methylindazolyl, benzofuranyl, benzothienyl, benzoxazolyl, benzothiazolyl, which may carry a divalent substituent such as methylenedioxy, difluoromethylenedioxy, chlorofluoromethylenedioxy, dichloromethylenedioxy in adjacent positions or may in each case be mono- to pentasubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, amino, $C_1$–$C_4$-monoalkylamino, $C_1$–$C_4$-dialkylamino, $C_3$–$C_6$-cycloalkyl, $C_1$–$C_4$-alkoxycarbonyl, $C_1$–$C_4$-alkoxycarbonyl-$C_1$–$C_4$-alkyl, hydroxyl, nitro or cyano;
is furyl, thienyl, pyrrolyl, isoxazolyl, isothiazolyl, pyrazolyl, oxazolyl, thiazolyl, imidazolyl, oxadiazolyl, thiadiazolyl, triazolyl, pyridinyl, pyridazinyl, pyrimidinyl, pyrazinyl or triazinyl, pyranyl or thiopyranyl which may in each case be mono- to trisubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, amino, $C_1$–$C_4$-monoalkylamino, $C_1$–$C_4$-dialkylamino, $C_3$–$C_6$-cycloalkyl, $C_1$–$C_4$-alkoxycarbonyl, $C_1$–$C_4$-alkoxycarbonyl-$C_1$–$C_4$-alkyl, hydroxyl, nitro or cyano;
have excellent microbicidal properties and can be used both in the protection of materials and in crop protection.

Particularly suitable for this use are compounds of the formula I in which
R[1] is hydrogen, $C_1$–$C_4$-alkyl which may be substituted by halogen, cyano, hydroxycarbonyl, $C_1$–$C_3$-alkoxy, $C_1$–$C_3$-alkylthio, $C_1$–$C_3$-alkoxycarbonyl, or is halogen and
R[2] is hydrogen.

Very particularly suitable are compounds of the formula I in which
R[1] is hydrogen or halogen;
R[2] is hydrogen and
A is phenyl, naphthyl, quinolyl, quinazolyl, quinoxalyl, benzofuranyl, benzothienyl, benzoxazolyl, benzothiazolyl, which may carry a divalent substituent such as methylenedioxy, difluoromethylenedioxy, chlorofluoromethylenedioxy in adjacent positions or may in each case be mono- to trisubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkoxycarbonyl, hydroxyl, nitro or cyano;
is furanyl, thienyl, pyrrolyl, isoxazolyl, isothiazolyl, pyrazolyl, oxazolyl, thiazolyl, imidazolyl, oxadiazolyl, pyridyl, pyranyl or thiopyranyl, each of which may be mono- to disubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkoxycarbonyl, nitro or cyano.

Depending on the substitution pattern, the compounds of the formula I may contain one or more chiral centers, in which case they are present as enantiomer or diastereomer mixtures. The invention provides both the use of the pure enantiomers or diastereomers and the use of the mixtures.

The present invention provides the novel nitroethane derivatives of the formula Ia

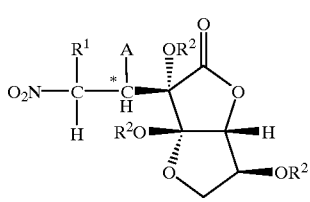

Ia in which
R[1] is $C_1$–$C_6$-alkyl which may be substituted by halogen, cyano, hydroxycarbonyl, $C_1$–$C_3$-alkoxy, $C_1$–$C_3$-alkylthio, $C_1$–$C_3$-alkoxycarbonyl, or is $C_3$–$C_6$-alkenyl, $C_3$–$C_6$-alkynyl, halogen, cyano or thiocyanato and
R[2] is hydrogen, formyl; halogen- or $C_1$–$C_3$-alkoxy-substituted or unsubstituted $C_1$–$C_6$-alkylcarbonyl, $C_2$–$C_6$-alkenylcarbonyl, $C_4$–$C_6$-alkyldienylcarbonyl or $C_2$–$C_6$-alkynylcarbonyl;
or
R[1] is hydrogen, $C_1$–$C_6$-alkyl which may be substituted by halogen, cyano, hydroxycarbonyl, $C_1$–$C_3$-alkoxy, $C_1$–$C_3$-alkylthio, $C_1$–$C_3$-alkoxycarbonyl, or is $C_3$–$C_6$-alkenyl, $C_3$–$C_6$-alkynyl, halogen, cyano or thiocyanato and
R[2] is formyl; halogen- or $C_1$–$C_3$-alkoxy-substituted or unsubstituted $C_1$–$C_6$-alkylcarbonyl, $C_2$–$C_6$- alkenylcarbonyl, $C_4$–$C_6$-alkyldienylcarbonyl or $C_2$–$C_6$-alkynylcarbonyl;
and in each case A is phenyl, naphthyl, quinolyl, quinazolyl, guinoxalyl, 1-methylindolyl, 1-methylbenzimidazolyl, 2-methylindazolyl, benzofuranyl, benzothienyl, benzoxazolyl, benzothiazolyl, which may carry a divalent substituent such as methylenedioxy, difluoromethylenedioxy, chlorofluoromethylenedioxy, dichloromethylenedioxy in adjacent positions or may in each case be mono- to pentasubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, amino, $C_1$–$C_4$-monoalkylamino, $C_1$–$C_4$-dialkylamino, $C_3$–$C_6$-cycloalkyl, $C_1$–$C_4$-alkoxycarbonyl, $C_1$–$C_4$-alkoxycarbonyl-$C_1$–$C_4$-alkyl, hydroxyl, nitro or cyano;
is furyl, thienyl, pyrrolyl, isoxazolyl, isothiazolyl, pyrazolyl, oxazolyl, thiazolyl, imidazolyl, oxadiazolyl, thiadiazolyl, triazolyl, pyridinyl, pyridazinyl, pyrimidinyl, pyrazinyl or triazinyl, pyranyl or thiopyranyl, which are in each case mono- to trisubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, amino, $C_1$–$C_4$-monoalkylamino, $C_1$–$C_4$-dialkylamino, $C_3$–$C_6$-cycloalkyl, $C_1$–$C_4$-alkoxycarbonyl, $C_1$–$C_4$-alkoxycarbonyl-$C_1$–$C_4$-alkyl, hydroxyl, nitro or cyano.

The present invention furthermore provides the novel substituted nitroethane derivatives of the formula Ib

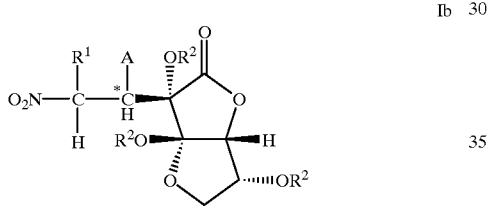

Ib in which $R^1$ is hydrogen, $C_1$–$C_6$-alkyl which may be substituted by halogen, cyano, hydroxycarbonyl, $C_1$–$C_3$-alkoxy, $C_1$–$C_3$-alkylthio, $C_1$–$C_3$-alkoxycarbonyl, or is $C_3$–$C_6$-alkenyl, $C_3$–$C_6$-alkynyl, halogen, cyano or thiocyanato;

$R^2$ is hydrogen, formyl; halogen- or $C_1$–$C_3$-alkoxy-substituted or unsubstituted $C_1$–$C_6$-alkylcarbonyl, $C_2$–$C_6$-alkenylcarbonyl, $C_4$–$C_6$-alkyldienylcarbonyl or $C_2$–$C_6$-alkynylcarbonyl and A is phenyl, naphthyl, quinolyl, quinazolyl, quinoxalyl, 1-methylindolyl, 1-methylbenzimidazolyl, 2-methylindazolyl, benzofuranyl, benzothienyl, benzoxazolyl, benzothiazolyl, which may carry a divalent substituent such as methylenedioxy, difluoromethylenedioxy, chlorofluoromethylenedioxy, dichloromethylenedioxy in adjacent positions or may in each case be mono- to pentasubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, amino, $C_1$–$C_4$-monoalkylamino, $C_1$–$C_4$-dialkylamino, $C_3$–$C_6$-cycloalkyl, $C_1$–$C_4$-alkoxycarbonyl, $C_1$–$C_4$-alkoxycarbonyl-$C_1$–$C_4$-alkyl, hydroxyl, nitro or cyano;
is furyl, thienyl, pyrrolyl, isoxazolyl, isothiazolyl, pyrazolyl, oxazolyl, thiazolyl, imidazolyl, oxadiazolyl, thiadiazolyl, triazolyl, pyridinyl, pyridazinyl, pyrimidinyl, pyrazinyl or triazinyl, pyranyl or thiopyranyl which may in each case be mono- to trisubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, amino, $C_1$–$C_4$-monoalkylamino, $C_1$–$C_4$-dialkylamino, $C_3$–$C_6$-cycloalkyl, $C_1$–$C_4$-alkoxycarbonyl, $C_1$–$C_4$-alkoxycarbonyl-$C_1$–$C_4$-alkyl, hydroxyl, nitro or cyano.

The terms alkyl, alkoxy, alkylthio, alkoxycarbonyl, alkenyl, alkynyl, haloalkyl, haloalkoxy, haloalkylthio, monoalkylamino, dialkylamino, cycloalkyl, alkoxycarbonylalkyl, alkylcarbonyl, alkenylcarbonyl, alkyldienylcarbonyl and alkynylcarbonyl used in the definition of the substituents $R^1$, $R^2$ and A are—like the term halogen—collective terms for individual enumerations of the individual group members. All alkyl moieties may be straight-chain or branched. The haloalkyl radical preferably carries one to five identical or different halogen atoms.

Examples of specific meanings are:

halogen: fluorine, chlorine, bromine and iodine, preferably fluorine and chlorine;

$C_1$–$C_3$-alkyl and the alkyl moieties of the radicals $C_1$–$C_3$-alkoxy, $C_1$–$C_3$-alkylthio, $C_1$–$C_3$-alkoxycarbonyl: methyl, ethyl, n-propyl, 1-methylethyl;

$C_1$–$C_4$-alkyl and the alkyl moieties of the radicals $C_1$–$C_4$-alkoxy, $C_1$–$C_4$-alkoxycarbonyl: methyl, ethyl, n-propyl, 1-methylethyl, n-butyl, 1-methylpropyl, 2-methylpropyl and 1,1-dimethylethyl;

$C_1$–$C_6$-alkyl: $C_1$–$C_4$-alkyl as mentioned above, and n-pentyl, 1-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

$C_3$–$C_4$-alkenyl: for example prop-1-en-1-yl, prop-2-en-1-yl, 1-methylethenyl, n-buten-1-yl, n-buten-2-yl, n-buten-3-yl, 1-methylprop-1-en-1-yl, 2-methylprop-1-en-1-yl, 1-methylprop-2-en-1-yl, 2-methylprop-2-en-1-yl;

$C_3$–$C_6$-alkenyl: $C_3$–$C_4$-alkenyl as mentioned above, and n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut- 1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl, preferably ethenyl and prop-2-en-1-yl;

$C_3$–$C_4$-alkynyl: for example prop-1-yn-1-yl, prop-2-yn-3-yl, n-but-1-yn-1-yl, n-but-1-yn-4-yl, n-but-2-yn-1-yl;

$C_3$–$C_6$-alkynyl: $C_3$–$C_4$-alkynyl as mentioned above, and n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-1-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl, 4-methylpent-2-yn-5-yl, preferably prop-2-yn-1-yl, 1-methylprop-2-yn-1-yl;

$C_1$–$C_4$-haloalkyl: $C_1$–$C_4$-alkyl as mentioned above which is partially or fully substituted by fluorine, chlorine and/or bromine, ie. for example chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichlorethyl, pentafluoroethyl and 3-chloropropyl, preferably trifluoromethyl;

$C_1$–$C_4$-haloalkoxy: for example $C_1$–$C_4$-alkoxy as mentioned above which is partially or fully substituted by fluorine, chlorine and/or bromine, ie. for example chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2 chloro-2,2-difluoroethoxy, 2,2-dichloro-2-fluoroethoxy, 2,2,2-trichloroethoxy and pentafluoroethoxy, preferably $C_1$–$C_2$-haloalkoxy such as trifluoromethoxy;

$C_1$–$C_4$-alkylthio: for example methylthio, ethylthio, n-propylthio, 1-methylethylthio, n-butylthio, 1-methylpropylthio, 2-methylpropylthio and 1,1-dimethylethylthio, preferably methylthio, ethylthio, methylethylthio;

$C_1$–$C_4$-haloalkylthio: for example chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio and pentafluoroethylthio, preferably $C_1$–$C_2$-haloalkylthio such as trifluoromethylthio;

($C_1$–$C_4$-alkoxy)carbonyl-$C_1$–$C_2$-alkyl: for example $C_1$–$C_4$-alkyl which is substituted by ($C_1$–$C_4$-alkoxy) carbonyl such as $COOCH_3$, $COOC_2H_5$, n-propoxycarbonyl, $COOCH(CH_3)_2$, n-butoxycarbonyl, 1-methylpropoxycarbonyl, 2-methylpropoxycarbonyl, ie. for example $CH_2$—$CO_2CH_3$, $CH_2$—$COOC_2H_5$, n-propoxycarbonylmethyl, $CH_2$—$COOCH(CH_3)_2$, n-butoxycarbonylmethyl, (1-methylpropoxycarbonyl)methyl, (2-methylpropoxycarbonyl)methyl, $CH_2$—$COOC(CH_3)_3$, 1-(methoxycarbonyl)ethyl, 1-(ethoxycarbonyl)ethyl, 1-(n-propoxycarbonyl)ethyl, 1-(1-methylethoxycarbonyl)ethyl, 1-(n-butoxycarbonyl)ethyl, 2-(methoxycarbonyl)ethyl, 2-(ethoxycarbonyl)ethyl, 2-(n-propoxycarbonyl)ethyl, 2-(1-methylethoxycarbonyl)ethyl, 2-(butoxycarbonyl)ethyl, 2-(1-methylpropoxycarbonyl)ethyl, 2-(2-methylpropoxycarbonyl)ethyl, 2-(1,1-dimethylethoxycarbonyl)ethyl;

($C_1$–$C_4$-alkoxy) carbonyl-$C_1$–$C_4$-alkyl: ($C_1$–$C_4$-alkoxy) carbonyl-$C_1$–$C_2$-alkyl as mentioned above, and 2-(methoxycarbonyl)propyl, 2-(ethoxycarbonyl)propyl, 2-(n-propoxycarbonyl)propyl, 2-(1-methylethoxycarbonyl)propyl, 2-(n-butoxycarbonyl)propyl, 2-(1-methylpropoxycarbonyl)propyl, 2-(2-methylpropoxycarbonyl)propyl, 2-(1,1-dimethylethoxycarbonyl)propyl, 3-(methoxycarbonyl)propyl, 3-(ethoxycarbonyl)propyl, 3-(n-propoxycarbonyl)propyl, 3-(1-methylethoxycarbonyl)propyl, 3-(n-butoxycarbonyl)propyl, 3-(1-methylpropoxycarbonyl)propyl, 3-(2-methylpropoxycarbonyl)propyl, 3-(1,1-dimethylethoxycarbonyl)propyl, 2-(methoxycarbonyl)butyl, 2-(ethoxycarbonyl)butyl, 2-(n-propoxycarbonyl)butyl, 2-(1-methylethoxycarbonyl)butyl, 2-(n-butoxycarbonyl)butyl, 2-(1-methylpropoxycarbonyl)butyl, 2-(2-methylpropoxycarbonyl)butyl, 2-(1,1-dimethylethoxycarbonyl)butyl, 3-(methoxycarbonyl)butyl, 3-(ethoxycarbonyl)butyl, 3-(n-propoxycarbonyl)butyl, 3-(1-methylethoxycarbonyl)butyl, 3-(n-butoxycarbonyl)butyl, 3-(1-methylpropoxycarbonyl)butyl, 3-(2-methylpropoxycarbonyl)butyl, 3-(1,1-dimethylethoxycarbonyl)butyl, 4-(methoxycarbonyl)butyl, 4-(ethoxycarbonyl)butyl, 4-(n-propoxycarbonyl)butyl, 4-(1-methylethoxycarbonyl)butyl, 4-(n-butoxycarbonyl)butyl, 4-(1-methylpropoxycarbonyl)butyl, 4-(2-methylpropoxycarbonyl)butyl or 4-(1,1-dimethylethoxycarbonyl)butyl, preferably $CH_2$—$COOCH_3$, $CH_2$—$COOC_2H_5$, 1-(methoxycarbonyl)ethyl or 1-(ethoxycarbonyl)ethyl;

$C_1$–$C_4$-monoalkylamino: for example methylamino, ethylamino, n-propylamino, isopropylamino, n-butylamino, isobutylamino or tert-butylamino;

di-($C_1$–$C_4$-alkyl)amino: for example $N(CH_3)_2$, $N(C_2H_5)_2$, N,N-dipropylamino, N,N-di-(1-methylethyl)amino, N,N-dibutylamino, N,N-di-(1-methylpropyl)amino, N,N-di-(2-methylpropyl)amino, N,N-di-(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(-methylethyl)-N-(-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)

amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino, preferably $N(CH_3)_2$ or $N(C_2H_5)_2$;

$C_3$–$C_6$-cycloalkyl: for example cyclopropyl, cyclobutyl, cyclopentyl, cyclohexyl;

$C_1$–$C_6$-alkylcarbonyl: for example $CO-CH_3$, $CO-C_2H_5$, $CO-n-C_3H_7$, $CO-CH(CH_3)_2$, $CO-n-C_4H_9$, $CO-CH(CH_3)-C_2H_5$, $CO-CH_2-CH(CH_3)_2$, $CO-C(CH_3)_3$, $CO-n-C_5H_{11}$, $CO-CH(CH_3)-n-C_3H_7$, $CO-n-C_6H_{13}$, preferably $CO-CH_3$ or $CO-C_2H_5$;

$C_2$–$C_6$-alkenylcarbonyl: for example $CO-CH=CH_2$, $CO-CH_2-CH=CH_2$, $CO-C(CH_3)=CH_2$, $CO-CH=CH-CH_3$, $CO-CH_2-CH=CH-CH_3$, $CO-CH(CH_3)-CH=CH_2$, $CO-CH_2-CH_2-CH=CH_2$, $CO-CH=C(CH_3)_2$, $CO-CH=CH-n-C_3H_7$, $CO-CH(CH_3)-CH=CH-CH_3$, $CO-C(CH_3)=CH-CH_2-CH_3$, $COCH(CH_3)-CH_2CH=CH_2$, $CO-CH=CH-n-C_4H_9$, $CO-CH=CH-CH(CH_3)-C_2H_5$, $CO-CH_2CH=CH-n-C_3H_7$, $CO-C(CH_3)=CH-n-C_3H_7$, preferably $CO-CH=CH_2$ or $CO-CH_2-CH=CH_2$;

$C_4$–$C_6$-alkyldienylcarbonyl: for example $CO-CH=CH-CH=CH-CH_3$, $CO-CH=CH-CH=CH_2$, $CO-CH=CH=CH_2-CH=CH_2$, $CO-CH_2-CH=CH-CH_2-CH=CH_2$, $CO-CH=CH-CH_2-CH=CH-CH_3$;

$C_2$–$C_6$-alkynylcarbonyl: for example $CO-C\equiv CH$, $CO-CH_2C\equiv CH$, $CO-C\equiv C-CH_3$, $CO-CH_2-C\equiv C-CH_3$, $CO-CH(CH_3)-C\equiv CH$, $CO-CH_2-CH_2-C\equiv CH$, $CO-C\equiv C-n-C_3H_7$, $CO-CH(CH_3)-C\equiv C-CH_3$, $CO-CH(CH_3)CH_2-C\equiv CH$, $CO-C\equiv C-n-C_4H_9$, $CO-C\equiv C-CH(CH_3)-C_2H_5$, $CO-CH_2-C\equiv C-n-C_3H_7$, preferably $CO-C\equiv CH$ or $CO-CH_2-C\equiv CH$;

naphthyl: 1- and 2-naphthyl;

among the hetero-fuzed aromatics, preference is given to: quinolyl such as 2-quinolyl, 3-quinolyl, 4-quinolyl, 5-quinolyl, 6-quinolyl, 7-quinolyl and 8-quinolyl, quinazolyl such as 2-quinazolyl, 4-quinazolyl, 5-quinazolyl, 6-quinazolyl, 7-quinazolyl, 8-quinazolyl, quinoxalyl such as 2-quinoxalyl, 5-quinoxalyl, 6-quinoxalyl, 1-methylindolyl such as 1-methylindol-2-yl, 1-methylindol-3-yl, 1-methylindol-4-yl, 1-methylindol-5-yl, 1-methylindol-6-yl, 1-methylindol-7-yl, 1-methylbenzimidazolyl such as 1-methylbenzimidazol-2-yl, 1-methylbenzimidazol-4-yl, 1-methylbenzimidazol-5-yl, 1-methylbenzimidazol-6-yl, 2-methylindazolyl such as 2-methylindazol-3-yl, 2-methylindazol-4-yl, 2-methylindazol-5-yl, 2-methylindazol-6-yl, 2-methylindazol-7-yl, benzofuranyl such as benzofuran-2-yl, benzofuran-3-yl, benzofuran-4-yl, benzofuran-5-yl, benzofuran-6-yl, benzofuran-7-yl, benzothienyl such benzothien-2-yl, benzothien-3-yl, benzothien-4-yl, benzothien-5-yl, benzothien-6-yl, benzothien-7-yl, benzoxazolyl such as benzoxazol-2-yl, benzoxazol-4-yl, benzoxazol-5-yl, benzoxazol-6-yl, benzoxazol-7-yl, benzothiazolyl such as benzothiazol-2-yl, benzothiazol-4-yl, benzothiazol-5-yl, benzothiazol-6-yl, benzothiazol-7-yl, particular preference is given to: 2-quinolyl, 5-quinolyl, 2-quinazolyl, 4-quinazolyl, 5-quinazolyl, 6-quinazolyl, 2-quinoxalyl, 5-quinoxalyl, 1-methylindol-2-yl, 1-methylindol-3-yl, 1-methylindol-6-yl, 1-methylbenzimidazol-2-yl, 2-methylindazolol-3-yl, benzofuran-2-yl, benzothian-2-yl, benzoxazol-2-yl, benzothiazol-2-yl;

Among the heteroaromatics, preference is given to the 5- and 6-membered heteroaromatics, ie. for example furyl such as 2-furyl and 3-furyl, thienyl such as 2-thienyl and 3-thienyl, pyrrolyl such as 2-pyrrolyl and 3-pyrrolyl, isoxazolyl such as 3-isoxazolyl, 4-isoxazolyl and 5-isoxazolyl, isothiazolyl such as 3-isothiazolyl, 4-isothiazolyl and 5-isothiazolyl, pyrazolyl such as 3-pyrazolyl, 4-pyrazolyl and 5-pyrazolyl, oxazolyl such as 2-oxazolyl, 4-oxazolyl and 5-oxazolyl, thiazolyl such as 2-thiazolyl, 4-thiazolyl and 5-thiazolyl, imidazolyl such as 2-imidazolyl and 4-imidazolyl, oxadiazolyl such as 1,2,4-oxadiazol-3-yl, 1,2,4-oxadiazol-5-yl and 1,3,4-oxadiazol-2-yl, thiadiazolyl such as 1,2,4-thiadiazol-3-yl, 1,2,4-thiadiazol-5-yl and 1,3,4-thiadiazol-2-yl, triazolyl such as 1,2,4-triazol-1-yl, 1,2,4-triazol-3-yl and 1,2,4-triazol-4-yl, pyridinyl such as 2-pyridinyl, 3-pyridinyl and 4-pyridinyl, pyridazinyl such as 3-pyridazinyl and 4-pyridazinyl, pyrimidinyl such as 2-pyrimidinyl, 4-pyrimidinyl and 5-pyrimidinyl, 2-pyranyl, 3-pyranyl, 4-pyranyl, 2-thiopyranyl, 3-thiopyranyl and 4-thiopyranyl, furthermore 2-pyrazinyl, 1,3,5-triazin-2-yl, 1,2,4-triazin-3-yl, 1,2,4-triazin-5-yl and 1,2,4-triazin-6-yl, in particular pyridyl, pyrimidyl, furyl and thienyl.

Examples of microbicidally active compounds of the formulae Ia and Ib are listed in Table A below.

TABLE A

Ia

Ib

| $R^1$ | A | $R^2$ |
|---|---|---|
| H | $C_6H_5$ | H |
| $CH_3$ | $C_6H_5$ | H |
| $C_2H_5$ | $C_6H_5$ | H |
| $n$-$C_3H_7$ | $C_6H_5$ | H |
| $i$-$C_3H_7$ | $C_6H_5$ | H |
| $n$-$C_4H_9$ | $C_6H_5$ | H |
| sec-$C_4H_9$ | $C_6H_5$ | H |
| $i$-$C_4H_9$ | $C_6H_5$ | H |
| $t$-$C_4H_9$ | $C_6H_5$ | H |
| H | 1-naphthyl | H |
| H | 2-furyl | H |
| H | 2-thienyl | H |
| Cl | $C_6H_5$ | H |
| Br | $C_6H_5$ | H |
| H | 4-F—$C_6H_4$ | H |

TABLE A-continued

Ia

Ib

| R¹ | A | R² |
|---|---|---|
| CH$_3$ | 4-F—C$_6$H$_4$ | H |
| C$_2$H$_5$ | 4-F—C$_6$H$_4$ | H |
| n-C$_3$H$_7$ | 4-F—C$_6$H$_4$ | H |
| i-C$_3$H$_7$ | 4-F—C$_6$H$_4$ | H |
| n-C$_4$H$_9$ | 4-F—C$_6$H$_4$ | H |
| sec-C$_4$H$_9$ | 4-F—C$_6$H$_4$ | H |
| i-C$_4$H$_9$ | 4-F—C$_6$H$_4$ | H |
| tert-C$_4$H$_9$ | 4-F—C$_6$H$_4$ | H |
| H | 2-quinolyl | H |
| H | 2-quinoxalyl | H |
| H | 2-quinazolyl | H |
| Cl | 4-F—C$_6$H$_4$ | H |
| Br | 4-F—C$_6$H$_4$ | H |
| H | 4-Cl—C$_6$H$_4$ | H |
| CH$_3$ | 4-Cl—C$_6$H$_4$ | H |
| C$_2$H$_5$ | 4-Cl—C$_6$H$_4$ | H |
| n-C$_3$H$_7$ | 4-Cl—C$_6$H$_4$ | H |
| i-C$_3$H$_7$ | 4-Cl—C$_6$H$_4$ | H |
| n-C$_4$H$_9$ | 4-Cl—C$_6$H$_4$ | H |
| sec-C$_4$H$_9$ | 4-Cl—C$_6$H$_4$ | H |
| i-C$_4$H$_9$ | 4-Cl—C$_6$H$_4$ | H |
| tert-C$_4$H$_9$ | 4-Cl—C$_6$H$_4$ | H |
| H | benzofuran-2-yl | H |
| H | benzothian-2-yl | H |
| H | benzooxazol-2y1 | H |
| Cl | 4-Cl—C$_6$H$_4$ | H |
| Br | 4-Cl—C$_6$H$_4$ | H |
| H | 4-CF$_3$—C$_6$H$_4$ | H |
| CH$_3$ | 4-CF$_3$—C$_6$H$_4$ | H |
| C$_2$H$_5$ | 4-CF$_3$—C$_6$H$_4$ | H |
| n-C$_3$H$_7$ | 4-CF$_3$—C$_6$H$_4$ | H |
| i-C$_3$H$_7$ | 4-CF$_3$—C$_6$H$_4$ | H |
| n-C$_4$H$_9$ | 4-CF$_3$—C$_6$H$_4$ | H |
| sec-C$_4$H$_9$ | 4-CF$_3$—C$_6$H$_4$ | H |
| i-C$_4$H$_9$ | 4-CF$_3$—C$_6$H$_4$ | H |
| tert-C$_4$H$_9$ | 4-CF$_3$—C$_6$H$_4$ | H |
| H | benzothiazol-2-yl | H |
| H | 2-pyrrolyl | H |
| H | 3-isoxazolyl | H |
| Cl | 4-CF$_3$—C$_6$H$_4$ | H |
| Br | 4-CF$_3$—C$_6$H$_4$ | H |
| H | 4-F$_2$CHO—C$_6$H$_4$ | H |
| CH$_3$ | 4-F$_2$CHO—C$_6$H$_4$ | H |
| C$_2$H$_5$ | 4-F$_2$CHO—C$_6$H$_4$ | H |
| n-C$_3$H$_7$ | 4-F$_2$CHO—C$_6$H$_4$ | H |
| i-C$_3$H$_7$ | 4-F$_2$CHO—C$_6$H$_4$ | H |
| n-C$_4$H$_9$ | 4-F$_2$CHO—C$_6$H$_4$ | H |
| sec-C$_4$H$_9$ | 4-F$_2$CHO—C$_6$H$_4$ | H |
| i-C$_4$H$_9$ | 4-F$_2$CHO—C$_6$H$_4$ | H |
| tert-C$_4$H$_9$ | 4-F$_2$CHO—C$_6$H$_4$ | H |
| H | 3-isothiazolyl | H |
| H | 3-pyrazolyl | H |
| H | 2-oxazolyl | H |
| Cl | 4-F$_2$CHO—C$_6$H$_4$ | H |
| Br | 4-F$_2$CHO—C$_6$H$_4$ | H |
| H | 4-CF$_3$O—C$_6$H$_4$ | H |
| CH$_3$ | 4-CF$_3$O—C$_6$H$_4$ | H |
| C$_2$H$_5$ | 4-CF$_3$O—C$_6$H$_4$ | H |
| n-C$_3$H$_7$ | 4-CF$_3$O—C$_6$H$_4$ | H |
| i-C$_3$H$_7$ | 4-CF$_3$O—C$_6$H$_4$ | H |
| n-C$_4$H$_9$ | 4-CF$_3$O—C$_6$H$_4$ | H |
| sec-C$_4$H$_9$ | 4-CF$_3$O—C$_6$H$_4$ | H |
| i-C$_4$H$_9$ | 4-CF$_3$O—C$_6$H$_4$ | H |
| tert-C$_4$H$_9$ | 4-CF$_3$O—C$_6$H$_4$ | H |
| H | 2-thiazolyl | H |
| H | 2-imidazolyl | H |
| H | 1,2,4-oxadiazol-3-yl | H |
| Cl | 4-CF$_3$O—C$_6$H$_4$ | H |
| Br | 4-CF$_3$O—C$_6$H$_4$ | H |
| H | 4-CH$_3$—C$_6$H$_4$ | H |
| CH$_3$ | 4-CH$_3$—C$_6$H$_4$ | H |
| C$_2$H$_5$ | 4-CH$_3$—C$_6$H$_4$ | H |
| n-C$_3$H$_7$ | 4-CH$_3$—C$_6$H$_4$ | H |
| i-C$_3$H$_7$ | 4-CH$_3$—C$_6$H$_4$ | H |
| n-C$_4$H$_9$ | 4-CH$_3$—C$_6$H$_4$ | H |
| sec-C$_4$H$_9$ | 4-CH$_3$—C$_6$H$_4$ | H |
| i-C$_4$H$_9$ | 4-CH$_3$—C$_6$H$_4$ | H |
| tert-C$_4$H$_9$ | 4-CH$_3$—C$_6$H$_4$ | H |
| H | 2-pyridyl | H |
| H | 2-pyranyl | H |
| H | 2-thiopyranyl | H |
| Cl | 4-CH$_3$—C$_6$H$_4$ | H |
| Br | 4-CH$_3$—C$_6$H$_4$ | H |
| H | 4-Br—C$_6$H$_4$ | H |
| CH$_3$ | 4-Br—C$_6$H$_4$ | H |
| C$_2$H$_5$ | 4-Br—C$_6$H$_4$ | H |
| n-C$_3$H$_7$ | 4-Br—C$_6$H$_4$ | H |
| i-C$_3$H$_7$ | 4-Br—C$_6$H$_4$ | H |
| n-C$_4$H$_9$ | 4-Br—C$_6$H$_4$ | H |
| sec-C$_4$H$_9$ | 4-Br—C$_6$H$_4$ | H |
| i-C$_4$H$_9$ | 4-Br—C$_6$H$_4$ | H |
| tert-C$_4$H$_9$ | 4-Br—C$_6$H$_4$ | H |
| H | 5-quinolyl | H |
| H | 4-quinazolyl | H |
| H | 5-quinoxalyl | H |
| Cl | 4-Br—C$_6$H$_4$ | H |
| Br | 4-Br—C$_6$H$_4$ | H |
| H | 4-NO$_2$—C$_6$H$_4$ | H |
| CH$_3$ | 4-NO$_2$—C$_6$H$_4$ | H |
| C$_2$H$_5$ | 4-NO$_2$—C$_6$H$_4$ | H |
| n-C$_3$H$_7$ | 4-NO$_2$—C$_6$H$_4$ | H |
| i-C$_3$H$_7$ | 4-NO$_2$—C$_6$H$_4$ | H |
| n-C$_4$H$_9$ | 4-NO$_2$—C$_6$H$_4$ | H |
| sec-C$_4$H$_9$ | 4-NO$_2$—C$_6$H$_4$ | H |
| i-C$_4$H$_9$ | 4-NO$_2$—C$_6$H$_4$ | H |
| tert-C$_4$H$_9$ | 4-NO$_2$—C$_6$H$_4$ | H |
| H | 3-furyl | H |
| H | 3-thienyl | H |

TABLE A-continued

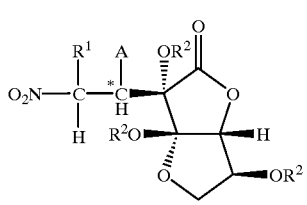

Ia

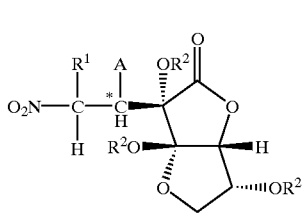

Ib

| R¹ | A | R² |
|---|---|---|
| H | 3-pyrrolyl | H |
| Cl | 4-NO₂—C₆H₄ | H |
| Br | 4-NO₂—C₆H₄ | H |
| H | 4-NC—C₆H₄ | H |
| CH₃ | 4-NC—C₆H₄ | H |
| C₂H₅ | 4-NC—C₆H₄ | H |
| n-C₃H₇ | 4-NC—C₆H₄ | H |
| i-C₃H₇ | 4-NC—C₆H₄ | H |
| n-C₄H₉ | 4-NC—C₆H₄ | H |
| sec-C₄H₉ | 4-NC—C₆H₄ | H |
| i-C₄H₉ | 4-NC—C₆H₄ | H |
| tert-C₄H₉ | 4-NC—C₆H₄ | H |
| H | 4-oxazolyl | H |
| H | 5-oxazolyl | H |
| H | 4-thiazolyl | H |
| Cl | 4-NC—C₆H₄ | H |
| Br | 4-NC—C₆H₄ | H |
| H | 4-CH₃—O—C₆H₄ | H |
| CH₃ | 4-CH₃—O—C₆H₄ | H |
| C₂H₅ | 4-CH₃—O—C₆H₄ | H |
| n-C₃H₇ | 4-CH₃—O—C₆H₄ | H |
| i-C₃H₇ | 4-CH₃—O—C₆H₄ | H |
| n-C₄H₉ | 4-CH₃—O—C₆H₄ | H |
| sec-C₄H₉ | 4-CH₃—O—C₆H₄ | H |
| i-C₄H₉ | 4-CH₃—O—C₆H₄ | H |
| tert-C₄H₉ | 4-CH₃—O—C₆H₄ | H |
| H | 5-thiazolyl | H |
| H | 3-pyridyl | H |
| H | 4-pyridyl | H |
| Cl | 4-CH₃—O—C₆H₄ | H |
| Br | 4-CH₃—O—C₆H₄ | H |
| H | 2,4-Cl₂—C₆H₃ | H |
| CH₃ | 2,4-Cl₂—C₆H₃ | H |
| C₂H₅ | 2,4-Cl₂—C₆H₃ | H |
| n-C₃H₇ | 2,4-Cl₂—C₆H₃ | H |
| i-C₃H₇ | 2,4-Cl₂—C₆H₃ | H |
| n-C₄H₉ | 2,4-Cl₂—C₆H₃ | H |
| sec-C₄H₉ | 2,4-Cl₂—C₆H₃ | H |
| i-C₄H₉ | 2,4-Cl₂—C₆H₃ | H |
| tert-C₄H₉ | 2,4-Cl₂—C₆H₃ | H |
| H | 2-pyranyl | H |
| H | 3-pyranyl | H |
| H | 4-pyranyl | H |
| Cl | 2,4-Cl₂—C₆H₃ | H |
| Br | 2,4-Cl₂—C₆H₃ | H |
| H | 2-Cl-4-NO₂—C₆H₃ | H |
| CH₃ | 2-Cl-4-NO₂—C₆H₃ | H |
| C₂H₅ | 2-Cl-4-NO₂—C₆H₃ | H |
| n-C₃H₇ | 2-Cl-4-NO₂—C₆H₃ | H |
| i-C₃H₇ | 2-Cl-4-NO₂—C₆H₃ | H |
| n-C₄H₉ | 2-Cl-4-NO₂—C₆H₃ | H |
| sec-C₄H₉ | 2-Cl-4-NO₂—C₆H₃ | H |
| i-C₄H₉ | 2-Cl-4-NO₂—C₆H₃ | H |
| tert-C₄H₉ | 2-Cl-4-NO₂—C₆H₃ | H |

TABLE A-continued

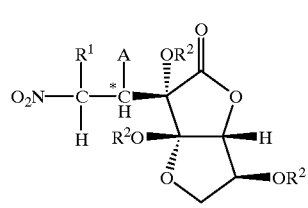

Ia

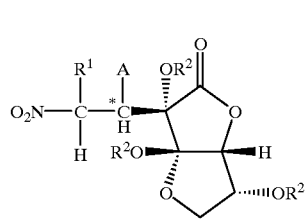

Ib

| R¹ | A | R² |
|---|---|---|
| H | 2-thiopyranyl | H |
| H | 3-thiopyranyl | H |
| H | 4-thiopyranyl | H |
| Cl | 2-Cl-4-NO₂—C₆H₃ | H |
| Br | 2-Cl-4-NO₂—C₆H₃ | H |
| H | 4-Cl—C₆H₄ | CH₃CO |
| CH₃ | 4-Cl—C₆H₄ | CH₃CO |
| C₂H₅ | 4-Cl—C₆H₄ | CH₃CO |
| n-C₃H₇ | 4-Cl—C₆H₄ | CH₃CO |
| i-C₃H₇ | 4-Cl—C₆H₄ | CH₃CO |
| n-C₄H₉ | 4-Cl—C₆H₄ | CH₃CO |
| sec-C₄H₉ | 4-Cl—C₆H₄ | CH₃CO |
| i-C₄H₉ | 4-Cl—C₆H₄ | CH₃CO |
| tert-C₄H₉ | 4-Cl—C₆H₄ | CH₃CO |
| H | 1,3,4-oxadiazol-2-yl | CH₃CO |
| H | 1,2,4-thiadiazol-3-yl | CH₃CO |
| H | 1,2,4-thiadiazol-5-yl | CH₃CO |
| Cl | 4-Cl—C₆H₄ | CH₃CO |
| Br | 4-Cl—C₆H₄ | CH₃CO |
| H | 4-NO₂—C₆H₄ | CH₃CO |
| CH₃ | 4-NO₂—C₆H₄ | CH₃CO |
| C₂H₅ | 4-NO₂—C₆H₄ | CH₃CO |
| n-C₃H₇ | 4-NO₂—C₆H₄ | CH₃CO |
| i-C₃H₇ | 4-NO₂—C₆H₄ | CH₃CO |
| n-C₄H₉ | 4-NO₂—C₆H₄ | CH₃CO |
| sec-C₄H₉ | 4-NO₂—C₆H₄ | CH₃CO |
| i-C₄H₉ | 4-NO₂—C₆H₄ | CH₃CO |
| tert-C₄H₉ | 4-NO₂—C₆H₄ | CH₃CO |
| H | 1,2,4-triazol-1-yl | CH₃CO |
| H | 3-pyridazinyl | CH₃CO |
| H | 2-pyrimidinyl | CH₃CO |
| Cl | 4-NO₂—C₆H₄ | CH₃CO |
| Br | 4-NO₂—C₆H₄ | CH₃CO |

In terms of microbicidal activity, preference is given to nitroethane derivatives of the formulae Ia and Ib

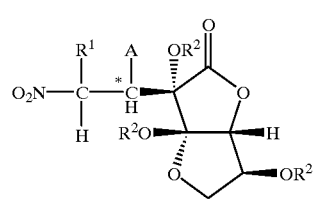

Ia

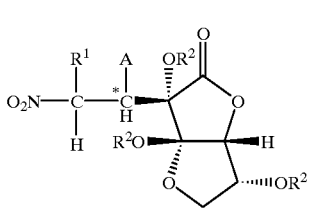
Ib having the following substituents, in each case preferably both on their own and in combination:

$R^1$ is a substituent selected from the group L1 to L 109,
$R^2$ is a substituent selected from the group P1 to P 84 and
A is a substituent selected from the group Q1 to Q 446

| Group No. | $R^1$ |
|---|---|
| L 1 | H |
| L 2 | $CH_3$ |
| L 3 | $C_2H_5$ |
| L 4 | $n-C_3H_7$ |
| L 5 | $i-C_3H_7$ |
| L 6 | $n-C_4H_9$ |
| L 7 | $sec-C_4H_9$ |
| L 8 | $i-C_4H_9$ |
| L 9 | $tert-C_4H_9$ |
| L 10 | $n-C_5H_{11}$ |
| L 11 | $sec-C_5H_{11}$ |
| L 12 | $i-C_5H_{11}$ |
| L 13 | $n-C_6H_{13}$ |
| L 14 | $sec-C_6H_{13}$ |
| L 15 | cyclopropyl |
| L 16 | cyclobutyl |
| L 17 | cyclopentyl |
| L 18 | cyclohexyl |
| L 19 | $CH_2CH_2Cl$ |
| L 20 | $(CH_2)_3Cl$ |
| L 21 | $CH(CH_3)CH_2Cl$ |
| L 22 | $(CH_2)_4Cl$ |
| L 23 | $C(CH_3)_2CH_2Cl$ |
| L 24 | $(CH_2)_5Cl$ |
| L 25 | $(CH_2)_6Cl$ |
| L 26 | $CH_2CN$ |
| L 27 | $(CH_2)_2CN$ |
| L 28 | $(CH_2)_3CN$ |
| L 29 | $CH(CH_3)CH_2CN$ |
| L 30 | $(CH_2)_4CN$ |
| L 31 | $C(CH_3)_2CH_2CN$ |
| L 32 | $(CH_2)_5CN$ |
| L 33 | $(CH_2)_6CN$ |
| L 34 | $CH(CH_3)CN$ |
| L 35 | $CH_2CO_2H$ |
| L 36 | $(CH_2)_2CO_2H$ |
| L 37 | $CH(CH_3)CO_2H$ |
| L 38 | $(CH_2)_3CO_2H$ |
| L 39 | $CH(CH_3)CH_2CO_2H$ |
| L 40 | $(CH_2)_4CO_2H$ |
| L 41 | $C(CH_3)_2CH_2CO_2H$ |
| L 42 | $(CH_2)_5CO_2H$ |
| L 43 | $(CH_2)_6CO_2H$ |
| L 44 | $CH_2OCH_3$ |
| L 45 | $(CH_2)_2OCH_3$ |
| L 46 | $(CH_2)_3OCH_3$ |
| L 47 | $CH(CH_3)CH_2OCH_3$ |
| L 48 | $(CH_2)_4OCH_3$ |
| L 49 | $C(CH_3)_2CH_2OCH_3$ |
| L 50 | $(CH_2)_5OCH_3$ |
| L 51 | $(CH_2)_6OCH_3$ |
| L 52 | $CH(CH_3)OCH_3$ |
| L 53 | $CH_2SCH_3$ |
| L 54 | $(CH_2)_2SCH_3$ |
| L 55 | $(CH_2)_3SCH_3$ |
| L 56 | $CH(CH_3)CH_2SCH_3$ |
| L 57 | $CH_2CO_2CH_3$ |
| L 58 | $(CH_2)_2CO_2CH_3$ |
| L 59 | $CH(CH_3)CO_2CH_3$ |
| L 60 | $CH_2CO_2C_2H_5$ |
| L 61 | $(CH_2)_2CO_2C_2H_5$ |
| L 62 | $CH(CH_3)CO_2C_2H_5$ |
| L 63 | $(CH_2)_3CO_2CH_3$ |
| L 64 | $CH(CH_3)CH_2CO_2CH_3$ |
| L 65 | $(CH_2)_4CO_2CH_3$ |
| L 66 | $C(CH_3)_2CH_2CO_2CH_3$ |
| L 67 | $(CH_2)_5CO_2CH_3$ |
| L 68 | $(CH_2)_6CO_2CH_3$ |
| L 69 | $CH_2CO_2-n-C_3H_7$ |
| L 70 | $(CH_2)_2CO_2-n-C_3H_7$ |
| L 71 | $CH(CH_3)CO_2-n-C_3H_7$ |
| L 72 | $(CH_2)_3CO_2-n-C_3H_7$ |
| L 73 | $CH(CH_3)CH_2CO_2-n-C_3H_7$ |
| L 74 | $(CH_2)_4CO_2-n-C_3H_7$ |
| L 75 | $C(CH_3)_2CO_2-n-C_3H_7$ |
| L 76 | $(CH_2)_5-CO_2-n-C_3H_7$ |
| L 77 | $(CH_2)_6CO_2-n-C_3H_7$ |
| L 78 | $CH_2-CH=CH_2$ |
| L 79 | $CH_2-CH=CH-CH_3$ |
| L 80 | $C(CH_3)=CH_2$ |
| L 81 | $CH(CH_3)CH=CH_2$ |
| L 82 | $C(CH_3)_2-CH=CH_2$ |
| L 83 | $CH_2-CH_2CH=CH_2$ |
| L 84 | $CH=CH-CH_3$ |
| L 85 | $C(CH_3)=CH-CH_3$ |
| L 86 | $CH_2-C(CH_3)=CH_2$ |
| L 87 | $CH_2-CH(CH_3)-CH=CH_2$ |
| L 88 | $CH(CH_3)-C(CH_3)=CH_2$ |
| L 89 | $C(C_2H_5)=CH-CH_3$ |
| L 90 | $CH(C_2H_5)-CH=CH_2$ |
| L 91 | $CH_2-CH=CH-n-C_3H_7$ |
| L 92 | $CH_2-C\equiv CH$ |
| L 93 | $CH_2-C\equiv C-CH$ |
| L 94 | $C\equiv C-CH_3$ |
| L 95 | $CH(CH_3)-C\equiv CH$ |
| L 96 | $C(CH_3)_2-C\equiv CH$ |
| L 97 | $CH_2-CH_2-C\equiv CH$ |
| L 98 | $CH_2CH(CH_3)-C\equiv CH$ |
| L 99 | $CH(C_2H_5)-C\equiv CH$ |
| L 100 | $CH_2-C\equiv C-n-C_3H_7$ |
| L 101 | $(CH_2)_2-C\equiv C-CH_3$ |
| L 102 | $(CH_2)_3-C\equiv CH$ |
| L 103 | $(CH_2)_4-C\equiv C-CH_3$ |
| L 104 | F |
| L 105 | Cl |
| L 106 | Br |
| L 107 | J |
| L 108 | CN |
| L 109 | SCN |
| | $R^2$ |
| P 1 | H |
| P 2 | HCO |
| P 3 | $CH_3CO$ |
| P 4 | $C_2H_5CO$ |
| P 5 | $n-C_3H_7CO$ |
| P 6 | $CH(CH_3)_2CO$ |
| P 7 | $C(CH_3)_3CO$ |
| P 8 | $CH(CH_3)_2CH_2CO$ |
| P 9 | $n-C_4H_9CO$ |
| P 10 | $C_2H_5-CH(CH_3)CO$ |
| P 11 | $n-C_5H_{11}CO$ |
| P 12 | $n-C_3H_7-CH(CH_3)CO$ |
| P 13 | $n-C_6H_{13}CO$ |
| P 14 | $CH_2=CH-CO$ |
| P 15 | $CH_2=CH-CH_2CO$ |
| P 16 | $CH_2=C(CH_3)CO$ |
| P 17 | $CH_3-CH=CH-CO$ |
| P 18 | $CH_3-CH=CH-CH_2CO$ |
| P 19 | $CH_2=CH-CH(CH_3)CO$ |
| P 20 | $CH_2=CH-(CH_2)_2CO$ |

-continued

| Group No. | |
|---|---|
| P 21 | $(CH_3)_2C=CH-CO$ |
| P 22 | $n-C_3H_7-CH=CH-CO$ |
| P 23 | $CH_3CH=CH-CH(CH_3)CO$ |
| P 24 | $C_2H_5-CH=C(CH_3)CO$ |
| P 25 | $CH_2=CH-CH_2-CH(CH_3)CO$ |
| P 26 | $n-C_4H_9-CH=CH-CO$ |
| P 27 | $HC\equiv C-CO$ |
| P 28 | $HC\equiv C-CH_2CO$ |
| P 29 | $CH_3-C\equiv C-CO$ |
| P 30 | $CH_3-C\equiv C-CH_2CO$ |
| P 31 | $HC\equiv C-CH(CH_3)CO$ |
| P 32 | $HC\equiv C-(CH_2)_2CO$ |
| P 33 | $n-C_3H_7-C\equiv C-CO$ |
| P 34 | $CH_3-C\equiv C-CH(CH_3)CO$ |
| P 35 | $HC\equiv C-CH_2-CH(CH_3)CO$ |
| P 36 | $n-C_4H_9-C\equiv C-CO$ |
| P 37 | $ClCH_2CO$ |
| P 38 | $Cl(CH_2)_2CO$ |
| P 39 | $Cl-CH(CH_3)CO$ |
| P 40 | $Cl(CH_2)_3CO$ |
| P 41 | $ClC(CH_3)_2CO$ |
| P 42 | $Cl(CH_2)_4CO$ |
| P 43 | $ClCH_2C(CH_3)_2CO$ |
| P 44 | $Cl_2CHCO$ |
| P 45 | $Cl_3CCO$ |
| P 46 | $F_2CH-CO$ |
| P 47 | $CF_3CO$ |
| P 48 | $C_2F_5-CO$ |
| P 49 | $FCH_2-CH_2CO$ |
| P 50 | $n-C_3F_7CO$ |
| P 51 | $n-C_4F_9CO$ |
| P 52 | $CF_3-CH_2CO$ |
| P 53 | $CF_3(CH_2)_2CO$ |
| P 54 | $CH_3OCH_2CO$ |
| P 55 | $C_2H_5OCH_2CO$ |
| P 56 | $n-C_3H_7OCH_2CO$ |
| P 57 | $i-C_3H_7OCH_2CO$ |
| P 58 | $CH_3O(CH_2)_2CO$ |
| P 59 | $C_2H_5O(CH_2)_2CO$ |
| P 60 | $CH_3OCH(CH_3)CO$ |
| P 61 | $C_2H_5OCH(C_2H_5)CO$ |
| P 62 | $CH_3OC(CH_3)_2CO$ |
| P 63 | $CH_3OCH_2C(CH_3)_2CO$ |
| P 64 | $C_2H_5OC(CH_3)_2CO$ |
| P 65 | $C_2H_5OCH_2C(CH_3)_2CO$ |
| P 66 | $CH_3O(CH_2)_3CO$ |
| P 67 | $C_2H_5O(CH_2)_3CO$ |
| P 68 | $CH_3O-CH=CH-CO$ |
| P 69 | $CH_3OCH_2-CH=CH-CO$ |
| P 70 | $C_2H_5OCH_2-CH=CH-CO$ |
| P 71 | $CH_3OC(CH_3)=CH-CO$ |
| P 72 | $CH_3OCH(CH_3)-CH=CH-CO$ |
| P 73 | $CH_3OCH=C(CH_3)CO$ |
| P 74 | $C_2H_5OCH=C(CH_3)CO$ |
| P 75 | $CH_3O-C\equiv C-CO$ |
| P 76 | $CH_3OCH_2-C\equiv C-CO$ |
| P 77 | $C_2H_5O-CH_2-C\equiv C-CO$ |
| P 78 | $CH_3OCH(CH_3)-C\equiv C-CO$ |
| P 79 | $CH_3O-C\equiv C-CH_2CO$ |
| P 80 | $CH_3-CH=CH-CH=CH-CO$ |
| P 81 | $CH_2=CH-CH=CH-CO$ |
| P 82 | $CH_2=CH-CH_2-CH=CH-CO$ |
| P 83 | $CH_2=CH-CH_2-CH=CH-CH_2-CO$ |
| P 84 | $CH_3-CH=CH-CH_2-CH=CH-CO$ |

TABLE B

| Group No. | A |
|---|---|
| Q 1 | $2-Cl-C_6H_4$ |
| Q 2 | $3-Cl-C_6H_4$ |
| Q 3 | $4-Cl-C_6H_4$ |
| Q 4 | $2-Br-C_6H_4$ |
| Q 5 | $3-Br-C_6H_4$ |

TABLE B-continued

| Group No. | A |
|---|---|
| Q 6 | $4-Br-C_6H_4$ |
| Q 7 | $2-F-C_6H_4$ |
| Q 8 | $3-F-C_6H_4$ |
| Q 9 | $4-F-C_6H_4$ |
| Q 10 | $2,3-Cl_2-C_6H_3$ |
| Q 11 | $2,4-Cl_2-C_6H_3$ |
| Q 12 | $2,5-Cl_2-C_6H_3$ |
| Q 13 | $2,6-Cl_2-C_6H_3$ |
| Q 14 | $3,4-Cl_2-C_6H_3$ |
| Q 15 | $3,5-Cl_2-C_6H_3$ |
| Q 16 | $2,3,4-Cl_3-C_6H_2$ |
| Q 17 | $2,3,5-Cl_3-C_6H_2$ |
| Q 18 | $2,4,6-Cl_3-C_6H_2$ |
| Q 19 | $3,4,5-Cl_3-C_6H_2$ |
| Q 20 | $2,3-F_2-C_6H_3$ |
| Q 21 | $2,4-F_2-C_6H_3$ |
| Q 22 | $2,5-F_2-C_6H_3$ |
| Q 23 | $2,6-F_2-C_6H_3$ |
| Q 24 | $2-Cl-4-F-C_6H_3$ |
| Q 25 | $2-Cl-4-Br-C_6H_3$ |
| Q 26 | $2-CH_3-C_6H_4$ |
| Q 27 | $3-CH_3-C_6H_4$ |
| Q 28 | $4-CH_3-C_6H_4$ |
| Q 29 | $2-C_2H_5-C_6H_4$ |
| Q 30 | $3-C_2H_5-C_6H_4$ |
| Q 31 | $4-C_2H_5-C_6H_4$ |
| Q 32 | $3-tert-C_4H_9-C_6H_4$ |
| Q 33 | $4-tert-C_4H_9-C_6H_4$ |
| Q 34 | $2,3-(CH_3)_2-C_6H_3$ |
| Q 35 | $3,4-(CH_3)_2-C_6H_3$ |
| Q 36 | $2,5-(CH_3)_2-C_6H_3$ |
| Q 37 | $2,6-(CH_3)_2-C_6H_3$ |
| Q 38 | $3,4-(CH_3)_2-C_6H_3$ |
| Q 39 | $3,5-(CH_3)_2-C_6H_3$ |
| Q 40 | $2,3,4-(CH_3)_3-C_6H_2$ |
| Q 41 | $2,3,5-(CH_3)_3-C_6H_2$ |
| Q 42 | $2,4,5-(CH_3)_3-C_6H_2$ |
| Q 43 | $2,4,6-(CH_3)_3-C_6H_2$ |
| Q 44 | $3,4,5-(CH_3)_3-C_6H_2$ |
| Q 45 | $2-CF_3-C_6H_4$ |
| Q 46 | $3-CF_3-C_6H_4$ |
| Q 47 | $4-CF_3-C_6H_4$ |
| Q 48 | $2-CN-C_6H_4$ |
| Q 49 | $3-CN-C_6H_4$ |
| Q 50 | $4-CN-C_6H_4$ |
| Q 51 | $2-OCH_3-C_6H_4$ |
| Q 52 | $3-OCH_3-C_6H_4$ |
| Q 53 | $4-OCH_3-C_6H_4$ |
| Q 54 | $2-OC_2H_5-C_6H_4$ |
| Q 55 | $3-OC_2H_5-C_6H_4$ |
| Q 56 | $4-OC_2H_5-C_6H_4$ |
| Q 57 | $2-O-n-C_3H_7-C_6H_4$ |
| Q 58 | $3-O-n-C_3H_7-C_6H_4$ |
| Q 59 | $4-O-n-C_3H_7-C_6H_4$ |
| Q 60 | $2-O-n-C_4H_9-C_6H_4$ |
| Q 61 | $2-O-i-C_3H_7-C_6H_4$ |
| Q 62 | $3-O-i-C_3H_7-C_6H_4$ |
| Q 63 | $4-O-i-C_3H_7-C_6H_4$ |
| Q 64 | $2,3-(OCH_3)_2-C_6H_3$ |
| Q 65 | $2,4-(OCH_3)_2-C_6H_3$ |
| Q 66 | $2,5-(OCH_3)_2-C_6H_3$ |
| Q 67 | $2,6-(OCH_3)_2-C_6H_3$ |
| Q 68 | $3,4-(OCH_3)_2-C_6H_3$ |
| Q 69 | $3,5-(OCH_3)_2-C_6H_3$ |
| Q 70 | $3,4,5-(OCH_3)_3-C_6H_2$ |
| Q 71 | $2-OCF_3-C_6H_4$ |
| Q 72 | $3-OCF_3-C_6H_4$ |
| Q 73 | $4-OCF_3-C_6H_4$ |
| Q 74 | $2-OCHF_2-C_6H_4$ |
| Q 75 | $3-OCHF_2-C_6H_4$ |
| Q 76 | $4-OCHF_2-C_6H_4$ |
| Q 77 | $2-OCF_2CHF_2-C_6H_4$ |
| Q 78 | $3-OCF_2CHF_2-C_6H_4$ |
| Q 79 | $4-OCF_2CHF_2-C_6H_4$ |
| Q 80 | $2-SCH_3-C_6H_4$ |
| Q 81 | $3-SCH_3-C_6H_4$ |
| Q 82 | $4-SCH_3-C_6H_4$ |

TABLE B-continued

| Group No. | A |
|---|---|
| Q 83 | 2-SC$_2$H$_5$—C$_6$H$_4$ |
| Q 84 | 3-SC$_2$H$_5$—C$_6$H$_4$ |
| Q 85 | 4-SC$_2$H$_5$—C$_6$H$_4$ |
| Q 86 | 2-S-i-C$_3$H$_7$—C$_6$H$_4$ |
| Q 87 | 3-S-i-C$_3$H$_7$—C$_6$H$_4$ |
| Q 88 | 4-S-i-C$_3$H$_7$—C$_6$H$_4$ |
| Q 89 | 2,4-(SCH$_3$)$_2$—C$_6$H$_3$ |
| Q 90 | 2-SCF$_3$—C$_6$H$_4$ |
| Q 91 | 3-SCF$_3$—C$_6$H$_4$ |
| Q 92 | 4-SCF$_3$—C$_6$H$_4$ |
| Q 93 | 2-NO$_2$—C$_6$H$_4$ |
| Q 94 | 3-NO$_2$—C$_6$H$_4$ |
| Q 95 | 4-NO$_2$—C$_6$H$_4$ |
| Q 96 | 2,3-(NO$_2$)$_2$—C$_6$H$_3$ |
| Q 97 | 2,4-(NO$_2$)$_2$—C$_6$H$_3$ |
| Q 98 | 2,5-(NO$_2$)$_2$—C$_6$H$_3$ |
| Q 99 | 2,6-(NO$_2$)$_2$—C$_6$H$_3$ |
| Q 100 | 3,4-(NO$_2$)$_2$—C$_6$H$_3$ |
| Q 101 | 3,5-(NO$_2$)$_2$—C$_6$H$_3$ |
| Q 102 | 2-Cl-4-NO$_2$—C$_6$H$_3$ |
| Q 103 | 2-Cl-4-CN—C$_6$H$_3$ |
| Q 104 | 2-CH$_3$-4-CN—C$_6$H$_3$ |
| Q 105 | 2-NH$_2$—C$_6$H$_4$ |
| Q 106 | 3-NH$_2$—C$_6$H$_4$ |
| Q 107 | 4-NH$_2$—C$_6$H$_4$ |
| Q 108 | 2-NHCH$_3$—C$_6$H$_4$ |
| Q 109 | 3-NHCH$_3$—C$_6$H$_4$ |
| Q 110 | 4-NHCH$_3$—C$_6$H$_4$ |
| Q 111 | 2-N(CH$_3$)$_2$—C$_6$H$_4$ |
| Q 112 | 3-N(CH$_3$)$_2$—C$_6$H$_4$ |
| Q 113 | 4-N(CH$_3$)$_2$—C$_6$H$_4$ |
| Q 114 | 4-cycl.-C$_3$H$_7$—C$_6$H$_4$ |
| Q 115 | 2-CO$_2$CH$_3$—C$_6$H$_4$ |
| Q 116 | 3-CO$_2$CH$_3$—C$_6$H$_4$ |
| Q 117 | 4-CO$_2$CH$_3$—C$_6$H$_4$ |
| Q 118 | 2-CO$_2$C$_2$H$_5$—C$_6$H$_4$ |
| Q 119 | 3-CO$_2$C$_2$H$_5$—C$_6$H$_4$ |
| Q 120 | 4-CO$_2$C$_2$H$_5$—C$_6$H$_4$ |
| Q 121 | 2-Cl-4-CO$_2$CH$_3$—C$_6$H$_4$ |
| Q 122 | 2-CH$_2$—CO$_2$CH$_3$—C$_6$H$_4$ |
| Q 123 | 3-CH$_2$—CO$_2$CH$_3$—C$_6$H$_4$ |
| Q 124 | 4-CH$_2$—CO$_2$CH$_3$—C$_6$H$_4$ |
| Q 125 | (2,3-OCF$_2$O)—C$_6$H$_3$ |
| Q 126 | (3,4-OCF$_2$O)—C$_6$H$_3$ |
| Q 127 | (2,3-OCFClO—)—C$_6$H$_3$ |
| Q 128 | (3,4-OCFClO—)—C$_6$H$_3$ |
| Q 129 | (2,3-OCCl$_2$O—)—C$_6$H$_3$ |
| Q 130 | (3,4-OCCl$_2$O—)—C$_6$H$_3$ |
| Q 131 | 1-naphthyl |
| Q 132 | 2-naphthyl |
| Q 133 | 2-chloro-1-naphthyl |
| Q 134 | 4-chloro-1-naphthyl |
| Q 135 | 2-methyl-1-naphthyl |
| Q 136 | 4-methyl-1-naphthyl |
| Q 137 | 5-methyl-1-naphthyl |
| Q 138 | 5-chloro-1-naphthyl |
| Q 139 | 8-methyl-1-naphthyl |
| Q 140 | 1-methyl-2-naphthyl |
| Q 141 | 1-chloro-2-naphthyl |
| Q 142 | 5-methyl-2-naphthyl |
| Q 143 | 2-quinolyl |
| Q 144 | 3-quinolyl |
| Q 145 | 4-quinolyl |
| Q 146 | 5-quinolyl |
| Q 147 | 6-quinolyl |
| Q 148 | 7-quinolyl |
| Q 149 | 8-quinolyl |
| Q 150 | 2-chloro-4-quinolyl |
| Q 151 | 2-methyl-4-quinolyl |
| Q 152 | 2-chloro-8-quinolyl |
| Q 153 | 2-methyl-8-quinolyl |
| Q 154 | 8-chloro-4-quinolyl |
| Q 155 | 8-methyl-4-quinolyl |
| Q 156 | 8-methoxy-4-quinolyl |
| Q 157 | 8-methoxy-2-quinolyl |
| Q 158 | 4-quinazolyl |
| Q 159 | 5-quinazolyl |
| Q 160 | 6-quinazolyl |
| Q 161 | 7-quinazolyl |
| Q 162 | 8-quinazolyl |
| Q 163 | 2-methyl-4-quinazolyl |
| Q 164 | 2-methyl-5-quinazolyl |
| Q 165 | 2-methyl-8-quinazolyl |
| Q 166 | 2-methoxy-4-quinazolyl |
| Q 167 | 2-methoxy-5-quinazolyl |
| Q 168 | 2-methoxy-8-quinazolyl |
| Q 169 | 2-quinoxalyl |
| Q 170 | 5-quinoxalyl |
| Q 171 | 6-quinoxalyl |
| Q 172 | 2-chloro-3-quinoxalyl |
| Q 173 | 2-chloro-5-quinoxalyl |
| Q 174 | 2-chloro-8-quinoxalyl |
| Q 175 | 2-methyl-3-quinoxalyl |
| Q 176 | 2-methyl-5-quinoxalyl |
| Q 177 | 2-methyl-8-quinoxalyl |
| Q 178 | 2-quinazolyl |
| Q 179 | 4-methyl-2-quinazolyl |
| Q 180 | 4-chloro-2-quinazolyl |
| Q 181 | 4-methoxy-2-quinazolyl |
| Q 182 | 5-methyl-2-quinazolyl |
| Q 183 | 8-chloro-2-quinazolyl |
| Q 184 | 8-methoxy-2-quinazolyl |
| Q 185 | 8-methyl-2-quinazolyl |
| Q 186 | 1-methyl-2-indolyl |
| Q 187 | 1-methyl-3-indolyl |
| Q 188 | 1-methyl-4-indolyl |
| Q 189 | 1-methyl-5-indolyl |
| Q 190 | 1-methyl-6-indolyl |
| Q 191 | 1-methyl-7-indolyl |
| Q 192 | 1,3-dimethyl-2-indolyl |
| Q 193 | 3-chloro-1-methyl-2-indolyl |
| Q 194 | 2-chloro-1-methyl-3-indolyl |
| Q 195 | 5-chloro-1-methyl-2-indolyl |
| Q 196 | 5-chloro-1-methyl-3-indolyl |
| Q 197 | 5,7-dichloro-1-methyl-2-indolyl |
| Q 198 | 5,7-dichloro-1-methyl-3-indolyl |
| Q 199 | 1-methyl-2-benzimidazolyl |
| Q 200 | 1-methyl-4-benzimidazolyl |
| Q 201 | 1-methyl-5-benzimidazolyl |
| Q 202 | 1-methyl-6-benzimidazolyl |
| Q 203 | 1,4-dimethyl-6-benzimidazolyl |
| Q 204 | 5-chloro-1-methyl-2-benzimidazolyl |
| Q 205 | 1,2-dimethyl-4-benzimidazolyl |
| Q 206 | 1-methyl-7-benzimidazolyl |
| Q 207 | 2-methyl-3-indazolyl |
| Q 208 | 2-methyl-4-indazolyl |
| Q 209 | 2-methyl-5-indazolyl |
| Q 210 | 2-methyl-6-indazolyl |
| Q 211 | 2-methyl-7-indazolyl |
| Q 212 | 2,5-dimethyl-3-indazolyl |
| Q 213 | 6-chloro-2-methyl-3-indazolyl |
| Q 214 | 2-benzofuranyl |
| Q 215 | 3-benzofuranyl |
| Q 216 | 4-benzofuranyl |
| Q 217 | 5-benzofuranyl |
| Q 218 | 6-benzofuranyl |
| Q 219 | 7-benzofuranyl |
| Q 220 | 3-methyl-2-benzofuranyl |
| Q 221 | 3-chloro-2-benzofuranyl |
| Q 222 | 2-methyl-3-benzofuranyl |
| Q 223 | 2-chloro-3-benzofuranyl |
| Q 224 | 2,4-dimethyl-3-benzofuranyl |
| Q 225 | 2-chloro-5-methyl-3-benzofuranyl |
| Q 226 | 2-methyl-5-chloro-3-benzofuranyl |
| Q 227 | 3-methoxy-2-benzofuranyl |
| Q 228 | 5-methoxy-6-benzofuranyl |
| Q 229 | 7-chloro-5-methoxy-2-benzofuranyl |
| Q 230 | 7-chloro-5-methoxy-3-benzofuranyl |
| Q 231 | 2-benzothienyl |
| Q 232 | 3-benzothienyl |
| Q 233 | 4-benzothienyl |
| Q 234 | 5-benzothienyl |
| Q 235 | 6-benzothienyl |
| Q 236 | 7-benzothienyl |

TABLE B-continued

| Group No. | A |
|---|---|
| Q 237 | 3-methyl-2-benzothienyl |
| Q 238 | 3-chloro-2-benzothienyl |
| Q 239 | 2-methyl-3-benzothienyl |
| Q 240 | 2-chloro-3-benzothienyl |
| Q 241 | 2,4-dimethyl-3-benzothienyl |
| Q 242 | 2-chloro-5-methyl-3-benzothienyl |
| Q 243 | 2-methyl-5-chloro-3-benzothienyl |
| Q 244 | 3-methoxy-2-benzothienyl |
| Q 245 | 5-methoxy-6-benzothienyl |
| Q 246 | 7-chloro-5-methoxy-2-benzothienyl |
| Q 247 | 7-chloro-5-methoxy-3-benzothienyl |
| Q 248 | 2-benzoxazolyl |
| Q 249 | 4-benzoxazolyl |
| Q 250 | 5-benzoxazolyl |
| Q 251 | 6-benzoxazolyl |
| Q 252 | 7-benzoxazolyl |
| Q 253 | 2-methyl-4-benzoxazolyl |
| Q 254 | 2-methyl-5-benzoxazolyl |
| Q 255 | 5-methyl-2-benzoxazolyl |
| Q 256 | 5-chloro-2-benzoxazolyl |
| Q 257 | 5-methoxy-2-benzoxazolyl |
| Q 258 | 5,7-dimethyl-2-benzoxazolyl |
| Q 259 | 7-chloro-5-methyl-2-benzoxazolyl |
| Q 260 | 7-methoxy-5-methyl-2-benzoxazolyl |
| Q 261 | 2-benzothiazolyl |
| Q 262 | 4-benzothiazolyl |
| Q 263 | 5-benzothiazolyl |
| Q 264 | 6-benzothiazolyl |
| Q 265 | 7-benzothiazolyl |
| Q 266 | 2-methyl-4-benzothiazolyl |
| Q 267 | 2-methyl-5-benzothiazolyl |
| Q 268 | 5-methyl-2-benzothiazolyl |
| Q 269 | 5-chloro-2-benzothiazolyl |
| Q 270 | 5-methoxy-2-benzothiazolyl |
| Q 271 | 5,7-dimethyl-2-benzothiazolyl |
| Q 272 | 7-chloro-5-methyl-2-benzothiazolyl |
| Q 273 | 7-methoxy-5-methyl-2-benzothiazolyl |
| Q 274 | 2-furyl |
| Q 275 | 3-furyl |
| Q 276 | 2-methyl-3-furyl |
| Q 277 | 3-methyl-2-furyl |
| Q 278 | 2-chloro-3-furyl |
| Q 279 | 3-chloro-2-furyl |
| Q 280 | 2,4-dimethyl-3-furyl |
| Q 281 | 2,5-dimethyl-3-furyl |
| Q 282 | 2-thienyl |
| Q 283 | 3-thienyl |
| Q 284 | 2-methyl-3-thienyl |
| Q 285 | 3-methyl-2-thienyl |
| Q 286 | 2-chloro-3-thienyl |
| Q 287 | 3-chloro-2-thienyl |
| Q 288 | 2,4-dimethyl-3-thienyl |
| Q 289 | 2,5-dimethyl-3-thienyl |
| Q 290 | 5-chloro-2-thienyl |
| Q 291 | 4-chloro-5-methyl-2-thienyl |
| Q 292 | 2-pyrrolyl |
| Q 293 | 3-pyrrolyl |
| Q 294 | 1-methyl-2-pyrrolyl |
| Q 295 | 3-chloro-1-methyl-2-pyrrolyl |
| Q 296 | 1,5-dimethyl-2-pyrrolyl |
| Q 297 | 3-isoxazolyl |
| Q 298 | 4-isoxazolyl |
| Q 299 | 5-isoxazolyl |
| Q 300 | 5-methyl-3-isoxazolyl |
| Q 301 | 5-methyl-3-isoxazolyl |
| Q 302 | 3-methyl-4-isoxazolyl |
| Q 303 | 3-methyl-5-isoxazolyl |
| Q 304 | 4,5-dimethyl-3-isoxazolyl |
| Q 305 | 3-isothiazolyl |
| Q 306 | 4-isothiazolyl |
| Q 307 | 5-isothiazolyl |
| Q 308 | 5-methyl-3-isothiazolyl |
| Q 309 | 5-methyl-3-isothiazolyl |
| Q 310 | 3-methyl-4-isothiazolyl |
| Q 311 | 3-methyl-5-isothiazolyl |
| Q 312 | 4,5-dimethyl-3-isothiazolyl |
| Q 313 | 3-pyrazolyl |
| Q 314 | 4-pyrazolyl |
| Q 315 | 1-methyl-3-pyrazolyl |
| Q 316 | 1-methyl-4-pyrazolyl |
| Q 317 | 5-pyrazolyl |
| Q 318 | 1-methyl-5-pyrazolyl |
| Q 319 | 1,4-dimethyl-3-pyrazolyl |
| Q 320 | 1,5-dimethyl-3-pyrazolyl |
| Q 321 | 1,5-dimethyl-4-pyrazolyl |
| Q 322 | 2-oxazolyl |
| Q 323 | 4-oxazolyl |
| Q 324 | 5-oxazolyl |
| Q 325 | 2-methyl-4-oxazolyl |
| Q 326 | 4-methyl-2-oxazolyl |
| Q 327 | 5-methyl-2-oxazolyl |
| Q 328 | 5-methyl-2-oxazolyl |
| Q 329 | 2-methyl-5-oxazolyl |
| Q 330 | 4,5-dimethyl-2-thiazolyl |
| Q 331 | 2-thiazolyl |
| Q 332 | 4-thiazolyl |
| Q 333 | 5-thiazolyl |
| Q 334 | 5-methyl-2-thiazolyl |
| Q 335 | 4-methyl-2-thiazolyl |
| Q 336 | 5-methyl-2-thiazolyl |
| Q 337 | 2-methyl-4-thiazolyl |
| Q 338 | 2-methyl-5-thiazolyl |
| Q 339 | 4,5-dimethyl-2-thiazolyl |
| Q 340 | 2-imidazolyl |
| Q 341 | 4-imidazolyl |
| Q 342 | 1-methyl-2-imidazolyl |
| Q 343 | 1-methyl-4-imidazolyl |
| Q 344 | 1-methyl-5-imidazolyl |
| Q 345 | 1,2-dimethyl-4-imidazolyl |
| Q 346 | 1,2-dimethyl-5-imidazolyl |
| Q 347 | 1,2,4-oxdiazol-3-yl |
| Q 348 | 1,2,4-oxdiazol-5-yl |
| Q 349 | 3-methyl-1,2,4-oxidiazol-5-yl |
| Q 350 | 1,3,4-oxdiazol-2-yl |
| Q 351 | 2-methyl-1,3,4-oxdiazol-5-yl |
| Q 352 | 1,2,4-thiadiazol-3-yl |
| Q 353 | 1,2,4-thiadiazol-5-yl |
| Q 354 | 3-methyl-1,2,4-thiadiazol-5-yl |
| Q 355 | 1,3,4-thiadiazol-2-yl |
| Q 356 | 2-methyl-1,3,4-thiadiazol-5-yl |
| Q 357 | 1,2,4-triazol-1-yl |
| Q 358 | 1,2,4-triazol-3-yl |
| Q 359 | 1-methyl-1,2,4-triazol-3-yl |
| Q 360 | 1-methyl-1,2,4-triazol-5-yl |
| Q 361 | 2-pyridinyl |
| Q 362 | 3-pyridinyl |
| Q 363 | 4-pyridinyl |
| Q 364 | 3-methyl-2-pyridinyl |
| Q 365 | 4-methyl-2-pyridinyl |
| Q 366 | 4-methyl-3-pyridinyl |
| Q 367 | 5-methyl-2-pyridinyl |
| Q 368 | 6-methyl-2-pyridinyl |
| Q 369 | 5,6-dimethyl-2-pyridinyl |
| Q 370 | 5,6-dimethyl-3-pyridinyl |
| Q 371 | 5,6-dimethyl-4-pyridinyl |
| Q 372 | 6-chloro-2-pyridinyl |
| Q 373 | 5,6,-dichloro-2-pyridinyl |
| Q 374 | 6-chloro-3-pyridinyl |
| Q 375 | 6-chloro-4-pyridinyl |
| Q 376 | 5-chloro-2-pyridinyl |
| Q 377 | 5-chloro-3-pyridinyl |
| Q 378 | 5-chloro-4-pyridinyl |
| Q 379 | 5-chloro-6-pyridinyl |
| Q 380 | 2-chloro-6-methyl-3-pyridinyl |
| Q 381 | 2-chloro-5-methyl-3-pyridinyl |
| Q 382 | 3-chloro-5-methyl-2-pyridinyl |
| Q 383 | 2-methoxy-3-chloro-6-pyridinyl |
| Q 384 | 3-pyridazinyl |
| Q 385 | 4-pyridazinyl |
| Q 386 | 6-methyl-3-pyridazinyl |
| Q 387 | 5-methyl-3-pyridazinyl |
| Q 388 | 5-methyl-4-pyridazinyl |
| Q 389 | 6-methyl-4-pyridazinyl |
| Q 390 | 6-chloro-3-pyridazinyl |

TABLE B-continued

| Group No. | A |
|---|---|
| Q 391 | 5-chloro-3-pyridazinyl |
| Q 392 | 5-chloro-4-pyridazinyl |
| Q 393 | 6-chloro-4-pyridazinyl |
| Q 394 | 6-methoxy-3-pyridazinyl |
| Q 395 | 2-pyrimidinyl |
| Q 396 | 4-pyrimidinyl |
| Q 397 | 5-pyrimidinyl |
| Q 398 | 2-methyl-4-pyrimidinyl |
| Q 399 | 2-methyl-5-pyrimidinyl |
| Q 400 | 2-chloro-4-pyrimidinyl |
| Q 401 | 2-chloro-5-pyrimidinyl |
| Q 402 | 2-methoxy-4-pyrimidinyl |
| Q 403 | 2-methoxy-5-pyrimidinyl |
| Q 404 | 4,6-dimethyl-2-pyrimidinyl |
| Q 405 | 4,6-dimethoxy-2-pyrimidinyl |
| Q 406 | 2-pyrazinyl |
| Q 407 | 2-methyl-3-pyrazinyl |
| Q 408 | 2-methyl-5-pyrazinyl |
| Q 409 | 2-methyl-6-pyrazinyl |
| Q 410 | 2-chloro-3-pyrazinyl |
| Q 411 | 2-chloro-5-pyrazinyl |
| Q 412 | 2-chloro-6-pyrazinyl |
| Q 413 | 2-methoxy-3-pyrazinyl |
| Q 414 | 2-methoxy-5-pyrazinyl |
| Q 415 | 2-methoxy-6-pyrazinyl |
| Q 416 | 1,3,5-triazin-2-yl |
| Q 417 | 4-methyl-1,3,5-triazin-2-yl |
| Q 418 | 6-methyl-1,3,5-triazin-2-yl |
| Q 419 | 4-methoxy-1,3,5-triazin-2-yl |
| Q 420 | 4,6-dimethyl-1,3,5-triazin-2-yl |
| Q 421 | 1,2,4-triazin-3-yl |
| Q 422 | 5-methyl-1,2,4-triazin-3-yl |
| Q 423 | 6-methyl-1,2,4-triazin-3-yl |
| Q 424 | 5-methoxy-1,2,4-triazin-3-yl |
| Q 425 | 6-methoxy-1,2,4-triazin-3-yl |
| Q 426 | 6-methyl-1,2,4-triazin-5-yl |
| Q 427 | 5-methyl-1,2,4-triazin-6-yl |
| Q 428 | 3-methyl-1,2,4-triazin-5-yl |
| Q 429 | 6-methoxy-1,2,4-triazin-5-yl |
| Q 430 | 5-methoxy-1,2,4-triazin-6-yl |
| Q 431 | 3-methoxy-1,2,4-triazin-5-yl |
| Q 432 | 3-methoxy-1,2,4-triazin-6-yl |
| Q 433 | 4-nitro-1-naphthyl |
| Q 434 | 2-nitro-1-quinolyl |
| Q 435 | 4-nitro-2-quinolyl |
| Q 436 | 3-nitro-2-furyl |
| Q 437 | 4-nitro-2-furyl |
| Q 438 | 4-nitro-3-furyl |
| Q 439 | 5-nitro-2-furyl |
| Q 440 | 3-nitro-2-thienyl |
| Q 441 | 4-nitro-2-thienyl |
| Q 442 | 4-nitro-3-thienyl |
| Q 443 | 5-nitro-3-thienyl |
| Q 444 | 3-nitro-2-pyridinyl |
| Q 445 | 5-nitro-2-pyridinyl |
| Q 446 | 5-nitro-3-pyridinyl |

In terms of their microbicidal activity, particular preference is furthermore given to the nitroethane derivatives of the formula I where the substituents have the following meanings:

$R^1$ is hydrogen, $C_1$–$C_4$-alkyl which may be substituted by halogen, cyano, hydroxycarbonyl, $C_1$–$C_3$-alkoxy, $C_1$–$C_3$-alkylthio, $C_1$–$C_3$-alkoxycarbonyl, or is halogen;

$R^2$ is hydrogen;

A is phenyl, napthyl, quinolyl, quinazolyl, quinoxalyl, 1-methylindolyl, 1-methylbenzimidazolyl, 2-methylindazolyl, benzofuranyl, benzothienyl, benzoxazolyl, benzothiazolyl, which may carry a divalent substituent such as methylenedioxy, difluoromethylenedioxy, chlorofluoromethylenedioxy, dichloromethylenedioxy in adjacent positions or may in each case be mono- to pentasubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, amino, $C_1$–$C_4$-monoalkylamino, $C_1$–$C_4$-dialkylamino, $C_3$–$C_6$-cycloalkyl, $C_1$–$C_4$-alkoxycarbonyl, $C_1$–$C_4$-alkoxycarbonyl-$C_1$–$C_4$-alkyl, hydroxyl, nitro or cyano;

is furyl, thienyl, pyrrolyl, isoxazolyl, isothiazolyl, pyrazolyl, oxazolyl, thiazolyl, imidazolyl, oxadiazolyl, thiadiazolyl, triazolyl, pyridinyl, pyridazinyl, pyrimidinyl, pyrazinyl or triazinyl, pyranyl or thiopyranyl, which may in each case be mono- to trisubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, amino, $C_1$–$C_4$-monoalkylamino, $C_1$–$C_4$-dialkylamino, $C_3$–$C_6$-cycloalkyl, $C_1$–$C_4$-alkoxycarbonyl, $C_1$–$C_4$-alkoxycarbonyl-$C_1$–$C_4$-alkyl, hydroxyl, nitro or cyano.

Particular preference is given to the nitroethane derivatives of the formula I where the substituents have the following meanings:

$R^1$ is hydrogen or halogen;

$R^2$ is hydrogen;

A is phenyl, naphthyl, quinolyl, quinazolyl, quinoxalyl, benzofuranyl, benzothienyl, benzoxazolyl, benzothiazolyl, which may in each case be mono- to trisubstituted, and furanyl, thienyl, pyrrolyl, isoxazolyl, isothiazolyl, pyrazolyl, oxazolyl, thiazolyl, imidazolyl, oxadiazolyl, pyridyl, pyranyl or thiopyranyl, which may in each case be mono- to disubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkoxycarbonyl, nitro or cyano.

Especially preferred are the nitroethane derivatives of the formula I where the substituents have the following meanings:

$R^1$ is halogen;

$R^2$ is hydrogen;

A is phenyl, naphthyl, quinolyl, quinazolyl, quinoxalyl, benzofuranyl, benzothienyl, benzoxazolyl, benzothiazolyl, which may in each case be mono- to trisubstituted, and furanyl, thienyl, pyrrolyl, isoxazolyl, isothiazolyl, pyrazolyl, oxazolyl, thiazolyl, imidazolyl, oxadiazolyl, pyridyl, pyranyl or thiopyranyl, which may in each case be mono- to disubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkoxycarbonyl, nitro or cyano.

Examples of particularly preferred nitroethane derivatives of the formula Ia and particularly preferred nitroethane derivatives of the formula Ib are compiled in Tables 1–4 and Tables 5–8, respectively.

Table 1

Nitroethane derivatives 1.001 to 1.446 of the formula Ia in which $R^1$ and $R^2$ are each hydrogen and A corresponds for each compound to one row of Table B

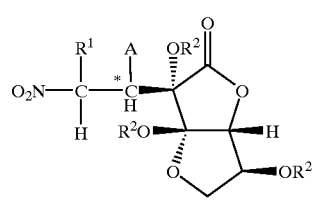

Ia

Table 2

Nitroethane derivatives 2.001 to 2.446 of the formula Ia in which $R^1$ is chlorine and $R^2$ is hydrogen and A corresponds for each compound to one row of Table B Table 3

Nitroethane derivatives 3.001 to 3.446 of the formula Ia in which $R^1$ is bromine and $R^2$ is hydrogen and A corresponds for each compound to one row of Table B Table 4

Nitroethane derivatives 4.001 to 4.446 of the formula Ia in which $R^1$ is hydrogen and $R^2$ is acetyl and A corresponds for each compound to one row of Table B Table 5

Nitroethane derivatives 5.001 to 5.446 of the formula Ib in which $R^1$ and $R^2$ are each hydrogen and A corresponds for each compound to one row of Table B

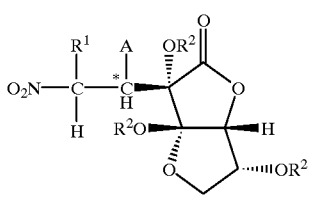

Ib

Table 6

Nitroethane derivatives 6.001 to 6.446 of the formula Ib in which $R^1$ is chlorine and $R^2$ is hydrogen and A corresponds for each compound to one row of Table B Table 7

Nitroethane derivatives 7.001 to 7.446 of the formula Ib in which $R^1$ is bromine and $R^2$ is hydrogen and A corresponds for each compound to one row of Table B Table 8

Nitroethane derivatives 8.001 to 8.446 of the formula Ib in which $R^1$ is hydrogen and $R^2$ is acetyl and A corresponds for each compound to one row of Table B The known and novel nitroethane derivatives of the formula I in which $R^1$, $R^2$ and A are each as defined above are obtained when nitrostyrenes of the formula II

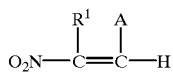

II in which $R^1$ and A are each as defined above are reacted with L-ascorbic acid of the formula IIIa

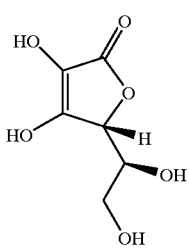

IIIa or D-isoascorbic acid of the formula IIIb

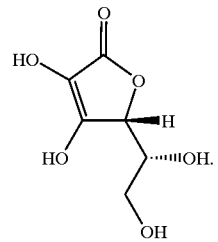

IIIb

The reaction of the nitrostyrenes II where $R^1$ is hydrogen and A is a chlorine-, hydroxyl-, methyl-, methoxy- or nitro-substituted phenyl radical with L-ascorbic acid IIIa is known (Pharmazie, 51 (1996), I, 11–16). The corresponding reactions with D-isoascorbic acid IIIb and the reactions of nitrostyrenes II, where $R^1$ is not hydrogen, with L-ascorbic acid IIIa and D-isoascorbic acid IIIb are novel.

The nitrostyrenes II are known, and they are easily obtainable by condensation of aldehydes with nitroalkanes according to the following literature references: Chem. Ber. 32 (1899) 1293–1295; Chem. Ber. 68 (1935) 184–192; Chem. Ber. 90 (1957) 1215–1225; J. Prakt. Chem., 137 (1933) 2, 339–344; J. Am. Chem. Soc., 56 (1934) 1556–1558; J. Am. Chem. Soc., 73 (1951) 4664–4666; J. Am. Chem. Soc., 78 (1956) 614–622; J. Org. Chem., 18 (1953) 1–3.

The preparation of the nitroethane derivatives Ia is described in scheme 1, using the reaction of β-bromonitrostyrene IIa and L-ascorbic acid IIIa as an example:

Scheme 1

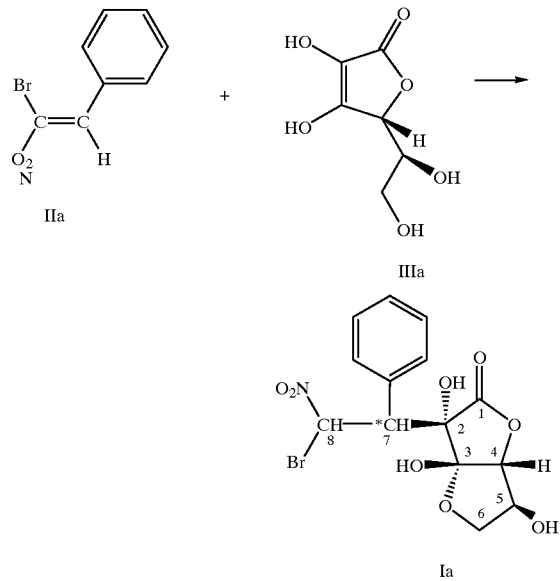

Correspondingly, the reaction with D-isoascorbic acid IIIb yields a similar compound Ib which differs from the compound Ia only in the position of the OH group at carbon atom 5.

The β-bromonitrostyrenes IIa are also known: Farmaco Ed. Sci., 30 (1975) 81–109; J. Amer. Chem. Soc., 73 (1951) 4664–4666.

The reaction of the nitrostyrenes II with L-ascorbic acid IIIa or D-isoascorbic acid IIIb is advantageously carried out in the presence of a solvent at from −10 to 150° C., preferably from 0 to 100° C., particularly preferably from 20 to 50° C.

The solvents that are used for these reactions are, depending on the temperature range, hydrocarbons such as toluene, xylene, chlorinated hydrocarbons such as 1,2-dichloroethane, 1,1,2,2-tetrachloroethane, chlorobenzene, 1,2-, 1,3-, or 1,4-dichlorobenzene, ethers such as 1,4-dioxane, anisole, glycol ethers such as dimethyl glycol ether, diethyl glycol ether, diethylene glycol dimethyl ether, esters such as ethyl acetate, propyl acetate, methyl isobutyrate, isobutyryl acetate, carboxamides such as DMF, N-methylpyrrolidone, nitrated hydrocarbons such as nitrobenzene, ureas such as tetraethylurea, tetrabutylurea, dimethylethyleneurea, dimethylpropyleneurea, sulfoxides such as dimethyl sulfoxide, sulfones such as dimethylsulfone, diethylsulfone, tetramethylenesulfone, nitriles such as acetonitrile, propionitrile, butyronitrile or isobutyronitrile; alcohols such as methanol, ethanol, n-propanol, isopranol, n-butanol, isobutanol or sec-butanol; water, or else mixtures of individual solvents, in particular mixtures of water with DMF, N-methylpyrrolidone, acetonitrile, methanol, ethanol or propanol and particularly preferably 40–80% strength aqueous ethanol.

The molar ratios at which the starting materials are reacted with each other are generally 0.9–2.2, preferably 0.95–1.8, particularly preferably 1–1.5, for the ratio of ascorbic acid III to nitrostyrene II. The concentration of the starting materials in the solvent is 0.1–5 mol/l, preferably 0.2–2 mol/l.

The nitrostyrene II is advantageously added over a period of 10 to 60 min at 20–40° C. to a mixture of the ascorbic acid III in one of the abovementioned solvents or solvent mixtures, and the mixture is then stirred for 10 to 120 hours at 20 to 100° C., preferably at 20–50° C., until the reaction has ended.

However, it is also possible to add the ascorbic acid III to a mixture of the nitrostyrene II in one of the abovementioned solvents or solvent mixtures and to complete the reaction as described above.

The reaction can be carried out under elevated pressure, continuously or batch-wise.

According to the formula I, the nitroethane derivatives may be mono- or polyacylated with respect to their radicals $R^2$, the selectivity and rate of acylation depending on the degree of steric hindrance. Preference is generally given to positions 5 and 2.

The acylation can be carried out under customary conditions, for example by reaction of a nitroethane derivative of the formula I in which $R^2$ is hydrogen with an acyl chloride or an acid anhydride in the presence of a base.

Suitable bases are alkali metal or alkaline earth metal bicarbonates, carbonates, hydroxides or else alkoxides. Preferred alkali metals and alkaline earth metals are lithium, sodium, potassium, calcium and magnesium. Preferred alkoxides are metal alkoxides of methanol, ethanol, n-propanol, isopropanol, n-butanol, isobutanol or sec-butanol.

The reaction can also be carried out in the presence of an organic phase, such as, for example, triethylamine, tri—n—propylamine, N-ethyldiisopropylamine, pyridine, α-, β, γ-picoline, 2,4-, 2,6-lutidine, N-methylpyrrolidone, triethylenediamine, dimethylaniline, N,N-dimethylcyclohexylamine, quinoline or acridine.

The acylation reaction is illustrated in scheme 2 by the reaction of α-L-xylo-3-hexulofuranosonic acid, 2-C-(2-nitro-1-phenyl-ethyl), γ-lactone and acetyl chloride.

Scheme 2

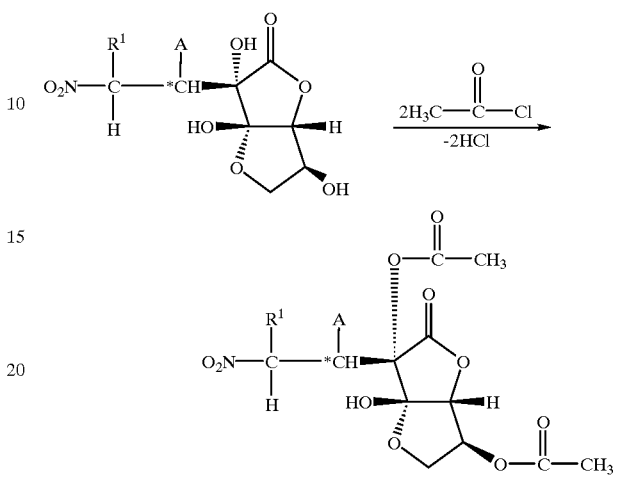

Suitable solvents are those mentioned above.

Generally 0.9–1.1, preferably 0.95–1.05, equivalents of acylating agent and base are employed per OH equivalent of the nitroethane derivative I. The concentration of the starting materials in the solvent is 0.01–5 mol/l, preferably 0.02–2 mol/l.

The acyl chloride or acid anhydride is advantageously added to a mixture of the hydroxynitroethane derivative I and the base over a period of 5–30 min, and the mixture is then stirred for another 1 to 30 hours, preferably 4 to 20 hours, at 15–70° C., preferably at 20–40° C., until the reaction has come to completion.

However, it is also possible to add the hydroxynitroethane derivative I and the base to a mixture of acylating agent and solvent and to complete the reaction as above.

It is also possible to use the appropriate carboxylic acids as acylating agents and to carry out the reaction as a customary esterification by removing the water of reaction azeotropically using a low-boiling solvent, by binding it chemically or by carrying out an extractive esterification.

Suitable dehydrating agents are conc. sulfuric acid and hydrogen chloride gas. Carbodiimides, for example dicyclohexylcarbodiimide, bind the water of reaction in a particularly gentle fashion.

The reaction can be accelerated by an acylation catalyst, for example by addition of a basic pyridine derivative such as 4-dimethylaminopyridine or 4-(1-pyrrolidinyl)pyridine. The molar amount of catalyst is from 0.001 to 20, preferably from 0.1 to 12, mol percent, based on the nitroethane derivative I.

Work-up of the reaction mixtures is usually carried out by known methods, for example by diluting the reaction solution with water and subsequent isolation of the product by filtration, crystallization or solvent extraction, or by removing the solvent, partitioning the residue in a mixture of water and a suitable organic solvent and work-up of the organic phase to give the product.

The active compounds of the formula I and the compositions according to the invention have strong microbicidal action and can be employed for controlling unwanted microorganisms. The active compounds of the formula I and the compositions according to the invention are suitable for protecting industrial materials against attack and destruction by unwanted microorganisms. Industrial materials are non-living materials as obtained in industrial processes or non-living materials intended for use in industry. Industrial materials to be protected by the active compounds I from being altered or destroyed by microbes are, for example, dispersions, adhesives, glues, cosmetics, starch solutions, wax emulsions, clay emulsions, paper, sizes, finishes, spin baths, textiles, leather, raw hides, gelatin preparations, bedding putty, joint fillers, wood, paints, articles made from plastic, coolants, drilling oils and other materials which can be attacked or decomposed by microorganisms. The compounds are further suitable for use as slimicides in the paper industry, in recooling plants and air humidifiers. The nitroethane derivatives I are particularly preferably employed in dispersions, such as polymer dispersions and paints.

Microorganisms which may cause a decomposition or an alteration of the industrial materials are, for example, spores, viruses, bacteria, fungi, yeasts, algae and slime organisms. The active compounds or preparations according to the invention preferably act against fungi, bacteria and algae.

By way of example, microorganisms of the following varieties may be mentioned:

*Alternaria alternata, Alternaria tenuis, Aspergillus niger, Aureobasidium pullulans, Candida albicans, Chaetomium globosum, Citrobacter freundii, Cladosporium resinae, Coniphora puetana, Desulfovibrio desulfuricans, Escherichia coli, Klebsielle pneumoniae, Lentinus tigrinus, Penicillium expansum, Penicillium funiculosum, Penicillium glaucum, Polyporus versicolor, Proteus mirabilis, Proteus vulgaris, Pseudomonas aeruginosa, Sclerophoma pityophilia, Saccharomyces cerevisiae, Staphylococcus aureus, Streptoverticillium rubrireticuli, Trichoderma viride.*

Depending on their physical and chemical properties and on the desired application, the active compounds of the formula I can be converted into customary formulations, for example solutions, emulsions, powders, pastes or dispersions.

These active compound formulations are prepared in a conventional manner, for example by mixing the active compounds with suitable extenders or solvents, if required by employing surfactants, ie. emulsifiers or dispersants. If water is used, organic solvents are generally employed as auxiliary solvents. Suitable solvents are, for example, alcohols, such as methanol, ethanol, propanol, butanol and cyclohexanol, or glycols, such as propylene glycol, 2-phenoxyethanol, phenoxypropanol, or aliphatic, cyclic and aromatic hydrocarbons, such as toluene, xylene, mesitylene, paraffin, tetrahydronaphthalene, alkylated naphthalenes or derivatves thereof, chlorobenzene, dichlorobenzene or strongly polar solvents, such as N,N-dimethylformamide, N,N-dimethylacetamide, dimethyl sulfoxide or N-methylpyrrolidone.

Suitable emulsifiers are, for example, alkali metal salts, alkaline earth metal salts or ammonium salts of aromatic sulfonic acids, for example of lignosulfonic acid, phenolsulfonic acid, naphthalenesulfonic acid and dibutylnaphthalenesulfonic acid, and of fatty acids, alkyl- and arylsulfonates, alkyl sulfates, lauryl ether sulfates and fatty alcohol sulfates, and salts of sulfated hexadecanols, heptadecanols and octadecanols, and condensation products of sulfonated naphthalene or naphthalene derivatives with formaldehyde, condensation products of naphthalene or of naphthalenesulfonic acids with phenol and formaldehyde, polyoxyethylene fatty alcohol ethers, polyoxyethylene octyl phenol ethers, ethoxylated isooctylphenol, ethoxylated octylphenol or ethoxylated nonylphenyl, alkylphenol polyglycol ethers, tributylphenyl polyglycol ethers, isotridecyl alcohol, alkylaryl polyglycol ethers, ethoxylated castor oil, polyoxyethylene alkyl ethers or polyoxypropylene alkyl ethers, lauryl alcohol polyglycol ether acetate, sorbitol esters; suitable dispersants are, for example, ligno-sulfite waste liquors and methylcellulose.

Aliphatic carboxylic acids may be added to improve the homogeneity of the concentrates. Such acids are, for example, propionic acid, hexanoic acid, heptanoic acid, branched carboxylic acids, such as 2-ethylenehexanoic acid, isooctanoic acid, neocarboxylic acids, aliphatic dicarboxylic acids, such as sebacic acid, cycloalkylcarboxylic acids, such as cyclohexanoic acid, arylcarboxylic acids, such as benzoic acid, 3- or 4-hydroxybenzoic acid.

Paints or precursors for preparing paints include plastic dispersions, dispersion paints for the paint industry, starch solutions, suspensions of other raw materials, such as color pigments or dyes or suspensions of fillers, such as kaolin, calcium carbonate, silicic acids, silica gels, silicates, talc, limestone, lime, chalk, bole, loess, clay, dolomite, diatomaceous earth, calcium sulfate and magnesium sulfate, magnesium oxide or ground plastics.

The activity and the spectrum of activity of the active compounds of the formula I or the compositions, intermediates or formulations preparable therefrom can be increased by adding further, optionally antimicrobially active compounds, bactericides, fungicides, herbicides, insecticides or other active compounds for widening the spectrum of activity or obtaining special effects. In many instances, this results in synergistic effects, ie. the spectrum of activity of the mixture is superior to the activity of the individual components.

Particularly advantageous mixing partners are, for example:

microbicides:

2-(thiocyanatomethylthio)benzothiazole, 1-[2-(2,4-dichlorophenyl)-2-(2-propenyloxy)ethyl]-1H-imidazole, 2,4,5,6-tetrachloroisophthalodinitrile, methylene bisthiocyanate, tributyltin oxide, tributyltin naphthenate, tributyltin benzoate, tributyltin salicylate, mercaptobenzothiazole, 1,2-benzisothiazolone and its alkali metal salts, alkali metal compounds of N'-hydroxy-N-cyclohexyldiazenium oxide, 2-(methoxycarbonylamino) benzimidazole, 2-methyl-3-oxo-5-chlorothiazolin-3-one, trihydroxymethylnitromethane, glutaraldehyde, chloroacetamide, polyhexamethylenebisguanides, 5-chloro-2-methyl-4-isothiazolin-3-one+magnesium salts, 2-methyl-4-isothiazolin-3-one, 3,5-dimethyltetrahydro-1,3,4-2H-thiadiazin-2-thione, hexahydrotriazine, N,N-methylolchloroacetamide, 2-n-octyl-4-isothiazolin-3-one, oxazolidines, bisoxazolidines, 5-dihydro-2,5-dialkoxy-2,5-dialkylfurans, diethyldodecylbenzylammonium chloride, dimethyloctadecyldimethylbenzylammonium chloride, dimethyldidecylammonium chloride, dimethyldidodecylammonium chloride, trimethyltetradecylammonium chloride, benzyldimethylalkyl-($C_{12}$–$C_{18}$)-ammonium chloride, dichlorobenzyldimethyldodecylammonium chloride, cetylpyridinium chloride, cetylpyridinium bromide, cetyltrimethylammonium chloride, laurylpyridinium chloride, laurylpyridinium bisulfate, benzyldodecyldi(beta-oxyethyl) ammonium chloride, dodecylbenzyltrimethylammonium chloride, n-alkyldimethylbenzylammonium chloride (alkyl radical: 40% $C_{12}$, 50% $C_{14}$, 10% $C_{16}$), lauryldimethylethylammonium ethyl sulfate, n-alkyldimethyl(1-naphthylmethyl)ammonium chloride (alkyl radical: 98% $C_{12}$, 2% $C_{14}$), cetyldimethylbenzylammonium chloride, lauryldimethylbenzylammonium chloride, Bactericides:
bronopol, dichlorophen, nitrapyrin, nickel dimethyldithiocarbamate, kasugamycin, octhilinone, furancarboxylic acid, oxytetracycline, probenazole, streptomycin, tecloftalam, copper sulfate and other copper preparations, Fungicides:
sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediamine-bis-dithiocarbamate, tetramethylthiuram disulfides, ammonia complex of zinc (N,N'-ethylene-bis-dithiocarbamate), ammonia complex of zinc (N,N'-propylene-bis-dithiocarbamate), zinc (N,N'-propylenebisdithiocarbamate), N,N'-polypropylenebis (thiocarbamoyl) disulfide;

nitro derivatives, such as dinitro-(1-methylheptyl)phenyl crotonate, 2-sec-butyl-4,6-dinitrophenyl-3,3-dimethyl acrylate, 2-sec-butyl-4,6-dinitrophenylisopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(furyl-(2)) benzimidazole, 2-(thiazolyl-(4))benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfuric diamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thio-1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine-4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine 2,2,2-trichloroethylacetal, piperazine-1,4-diylbis-(1-(2,2,2-trichloroethyl) formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, (2-chlorophenyl)-(4-chlorophenyl)-5-pyrimidine-methanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, [2-(4-chlorophenyl)ethyl]-(1,1-dimethylethyl)-1H-1,2,4-triazole-1-ethanol, 1-[3-(2-chlorophenyl)-1-(4-fluorophenyl)oxiran-2-ylmethyl]-1H-1,2,4-triazole, and a variety of fungicides, such as dodecylguanidine acetate, 3-[3-(3,5-dimethyl-2-oxycyclohexyl)-2-hydroxyethyl] glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-iso-propylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl) pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis-(4-fluorophenyl) methylsilyl)methyl)-1H-1,2,4-triazole.

Strobilurins, such as methyl E-methoximino-[α-(o-tolyloxy)-o-tolyl]acetate, methyl E-2-{2-[6-(2-cyanophenoxy)pyridimin-4-yloxy]phenyl}-3-methoxy-acrylate, methyl-E-methoximino-[α-(2-phenoxyphenyl)] acetamide, methyl-E-methoximino-[α-(2,5-dimethylphenoxy)-o-tolyl]acetamide.

Anilinopyrimidines, such as N-(4,6-dimethylpyrimidin-2-yl)aniline, N-[4-methyl-6-(1-propynyl)pyrimidin-2-yl] aniline, N-(4-methyl-6-cyclopropylpyrimidin-2-yl)aniline.

Phenylpyrroles, such as 4-(2,2-difluoro-1,3-benzodioxol-4-yl)pyrrole-3-carbonitrile.

Cinnamamides, such as 3-(4-chlorophenyl)-3-(3,4-dimethoxyphenyl)acryloylmorpholide.

Conazoles, such as (2RS,3SR)-1-[3-(2-chlorophenyl)-2-[4-fluorophenyl]oxiran-2-ylmethyl]-1H-1,2,4-triazole.

Insecticides:
abamectin, acephate, acrinathrin, alanycarb, aldicarb, alphamethrin, amitraz, avermectin, azadirachtin, azinphos A, azinphos M, azocyclotin, *Bacillus thuringiensis*, bendiocarb, benfuracarb, bensultap, beta-cyluthrin, bifenthrin, BPMC, brofenprox, bromophos A, bufencarb, buprofezin, butocarboxim, butylpyridaben, cadusafos, carbaryl, carbofuran, carbophenothion, carbosulfan, cartap, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cypromazin, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazofos, isofenphos, isoprocarb, isoxathion, ivemectin, lamda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, nitenpyram, omethoate, oxamyl, oxydemethone M, oxydeprofos, parathion A, parathion M, permethrin, phenthoate, phorate, phosalone, phosmet, phosphamdon, phoxim, pirimicarb, pirimiphos M, primiphos A, profenofos, promecarb, propaphos, propoxur, prothiofos, prothoate, pymetrozine, pyraclofos, pyradaphenthion, pyresmethrin, pyrethrum, pyridaben, pyrimidifen, pyriproxifen, quinalphos, salithion, sebufos, silafluofen, sulfotep, sulprofos, tebufenozide, tebufenpyrad, tebupirimfos, teflubenzuron, tefluthrin, temephos, terbam, terbufos, tetrachlorvinphos, thiafenox, thiodicarb, thiofanox, thiomethon, thionazin, thuringiensin, tralomethrin, triarathene, triazophos, triazuron, trichlorfon, triflumuron, trimethacarb, vamidothion, XMC, xylylcarb, zetamethrin.

Further suitable mixing partners are algicides, molluscicides, and active compounds against sea animals which colonize, for example, ship's bottom paints.

Examples of such preparations are:

Examples of formulations in dispersion paints or plastic dispersions:

a) 1000 parts by weight of a polymer dispersion based on polyacrylate are initially introduced and admixed with stirring with 0.25 parts by weight of a 20% strength by weight suspension concentrate of compound No. Ib.007 of Table 11 in propylene carbonate.

b) A solution of 3% by weight of compound No. Ia.034 of Table 9 in propylene glycol, dipropylene glycol, phenoxyethanol, phenoxypropanol or polyethylene glycol is suitable for incorporation into aqueous and solvent-containing plastic dispersions.

c) A water- or glycol-based paste containing 20 to 50% by weight of compound No. Ib.007 of Table 11 is suitable for incorporation into aqueous and solvent-containing plastic dispersions.

d) A solution of 90 parts by weight of compound No. Ia.064 of Table 10 and 10 parts by weight of N-methylpyrrolidone is suitable for incorporation into aqueous and solvent-containing plastic dispersions.

e) An aqueous dispersion of 20 parts by weight of compound No. Ia.034 of Table 9, 25 parts by weight of cyclohexanol, 65 parts by weight of a mineral oil fraction of boiling point 210–280° C. and 10 parts by weight of the addition product of 40 mol of ethylene oxide to 1 mol of castor oil. The mixture of this dispersion with 100,000 parts by weight of an aqueous paint dispersion comprises 0.02% of the active compound.

A mixture of 14 parts by weight of $Cu(OH)_2CuCO_3$, 33 parts by weight of monoethanolamine, 22 parts by weight of benzoic acid, 11 parts by weight of water, 4 parts by weight of compound No. Ia.034 of Table 9, 10 parts by weight of ethoxylated nonylphenol and 6 parts by weight of propylene glycol is particularly suitable for impregnating wood.

The microbicidal compositions or concentrates employed for protecting industrial materials comprise the active compound or the active compound combination in a concentration from 0.01 to 95, preferably 0.1 to 50% by weight.

The application concentration of the active compounds to be used depends on the species and the occurrence of the microorganisms to be controlled, and on the composition of the material to be protected. The application concentrations are generally in the range from 0.001 to 5% by weight, preferably from 0.05 to 1% by weight, based on the material to be protected.

The following examples illustrate the invention:

Biological Examples:

1. Microtiter Plate Test—250 ppm of a.s.

The active compound Ia.034, Table 9, was dissolved in acetone. 100 µl of a culture medium were placed in the wells of microtiter plates and aliquots of the active compound stock solution were pipetted in to give the desired test concentration. The final acetone concentration was 10%. Test microorganisms used were (bacteria) *Citrobacter freundii, Escherichia coli, Proteus mirabilis, Pseudomonas aeruginosa* and *Staphylococcus aureus*, (yeasts) *Candida albicans* and *Saccharomyces cerevisiae*, and (fungi) *Alternaria alternata, Aspergillus niger* and *Penicillium funciculosum*. The innoculated plates were incubated at 23° C. (yeasts and fungi) or 30° C. (bacteria). The growth of the microorganisms was evaluated after 2 (bacteria), 3 (yeasts) or 5 days (fungi):

| Test organism | Concentration in ppm active substance (a.s.) |
|---|---|
| | 250 |
| *Citrobacter freundii* | 0 |
| *Escherichia coli* | 0 |
| *Proteus mirabilis* | 0 |
| *Pseudomonas Aeruginosa* | 0 |
| *Staphylococcus aureus* | 0 |
| *Candida albicans* | 0 |
| *Saccharomyces cerevisiae* | 0 |
| *Alternaria alternata* | 0 |
| *Aspergillus niger* | 0 |
| *Penicillium funiculosum* | 0 |
| Control | 5 |

0 = no growth
5 = no action, growth as in control

0=no growth
5=no action, growth as in control

2. Preservation Stress Test in a Polymer Dispersion Based on Polyacrylate

In-depth tests were carried out in a polymer dispersion based on polyacrylate. The active compound Ia.034, Table 9, was dissolved in acetone and admixed to the dispersion in concentrations of 500, 250 and 100 ppm of a.s. The dispersions were then inoculated ("stressed") with a mixture of microorganisms. The mixture comprised the microorganisms mentioned under point 1. The batches were incubated at 23° C. and inoculated again every 7 days. After 6 cycles, the microorganism content of the dispersion was determined.

It was found that the polymer dispersion could be kept free of microorganisms using an application concentration of 500 ppm of a.s.

Furthermore, the compounds I have good activity against phytopathogenic fungi, in particular from the classes of the Ascomycetes, Deuteromycetes, Phycomycetes and Basidiomycetes.

They are especially important for controlling a large number of fungi on a variety of crop plants such as wheat, rye, barley, oats, rice, maize, grass, bananas, cotton, soya, coffee, sugarcane, grapevines, fruit species, ornamentals and vegetables such as cucumbers, beans, tomatoes, potatoes and cucurbits, and on the seeds of these plants.

Specifically, they are suitable for controlling the following plant diseases: *Erysiphe graminis* (powdery mildew) in cereals, *Erysiphe cichoracearum* and *Sphaerotheca fuliginea* on cucurbits, *Podosphaera leucotricha* on apples, *Uncinula necator* on grapevines, *Puccinia* species on cereals, *Rhizoctonia* species on cotton, rice and lawn, *Ustilago* species on cereals and sugarcane, *Venturia inaequalis* (scab) on apples, *Helminthosporium* species on cereals, *Septoria nodorum* on wheat, *Botrytis cinerea* (gray mold) on strawberries, vegetables, ornamentals and grapevines, *Cercospora arachidicola* on groundnuts, *Pseudocercosporella herpotrichoides* on wheat, barley, *Pyricularia oryzae* on rice, *Phytophthora infestans* on potatoes and tomatoes, Fusarium and *Verticillium* species on various plants, *Plasmopara viticola* on grapevines, *Pseudoperonospera* species on hops and cucumbers, *Alternaria* species on vegetables and fruit, and *Mycosphaerella* species on bananas.

The compounds I are applied by treating the fungi, or the plants, seeds, materials or the soil to be protected against fungal infection, with a fungicidally effective amount of the active compounds. Application is carried out before or after infection of the materials, plants or seeds by the fungi.

The compounds can be converted into customary formulations, such as solutions, emulsions, suspensions, dusts, powders, pastes and granules.

In general, the fungicidal compositions comprise from 0.1 to 95, preferably 0.5 to 90% by weight of active compound.

When used in crop protection, the rates of application are from 0.01 to 2.0 kg of active compound per ha, depending on the nature of the effect desired.

In the treatment of seed, amounts of active compound of from 0.001 to 0.1 g, preferably 0.01 to 0.05 g, are generally required per kilogram of seed.

When used in the protection of materials or stored products, the rate of application of active compound depends on the nature of the field of application and of the effect desired. Rates of application conventionally used in the protection of materials are, for example, from 0.001 g to 2 kg, preferably 0.005 g to 1 kg, of active compound per cubic meter of material treated.

In the use form as fungicides, the compositions according to the invention can also be present in combination with other active compounds, for example with herbicides, insecticides, growth regulators, fungicides or else with fertilizers.

In many cases, a mixture with fungicides results in a broader fungicidal spectrum of activity.

The active compounds can be applied as such, in the form of their formulations or in the application forms prepared therefrom, for example in the form of directly sprayable solutions, powders, suspensions or dispersions, emulsions, oil dispersions, pastes, dusts, compositions for broadcasting, or granules, by spraying, atomizing, dusting, broadcasting or watering. The application forms depend entirely on the intended uses; in any case, they should guarantee a very fine dispersion of the active compounds according to the invention.

The active compound concentrations in the ready-to-use preparations can be varied within relatively wide ranges.

In general, they are from 0.0001 to 10%, preferably from 0.01 to 1%.

It is also possible to use the active compounds with good success in the ultra-low-volume method (ULV), it being possible to apply formulations comprising more than 95% by weight of active compound or even the active compound without additives.

For controlling pests under outdoor conditions, the active compound application rate is from 0.1 to 2.0, preferably from 0.2 to 1.0, kg/ha.

In general, the formulations comprise from 0.01 to 95% by weight, preferably from 0.1 to 90% by weight, of the active compound. The active compounds are employed in a purity of from 90% to 100%, preferably from 95% to 100% (according to the NMR spectrum).

EXAMPLES OF FORMULATIONS ARE:

I. 5 parts by weight of a compound according to the invention are thoroughly mixed with 95 parts by weight of finely divided kaolin. This affords a dusting composition comprising 5% by weight of the active compound.

II. 30 parts by weight of a compound according to the invention are thoroughly mixed with a mixture of 92 parts by weight of pulverulent silica gel and 8 parts by weight of paraffin oil which had been sprayed onto the surface of this silica gel. This affords an active compound preparation having good adhesive properties (active compound content 23% by weight).

III. 10 parts by weight of a compound according to the invention are dissolved in a mixture comprising 90 parts by weight of xylene, 6 parts by weight of the addition product of 8 to 10 mol of ethylene oxide to 1 mol of oleic acid N-monoethanolamide, 2 parts by weight of the calcium salt of dodecylbenzenesulfonic acid and 2 parts by weight of the addition product of mol of ethylene oxide to 1 mol of castor oil (active compound content 9% by weight).

IV. 20 parts by weight of a compound according to the invention are dissolved in a mixture comprising 60 parts by weight of cyclohexanone, 30 parts by weight of isobutanol, 5 parts by weight of the addition product of 7 mol of ethylene oxide to 1 mol of isooctylphenol and 5 parts by weight of the addition product of mol of ethylene oxide to 1 mol of castor oil (active compound content 16% by weight).

V. 80 parts by weight of a compound according to the invention are mixed well with 3 parts by weight of the sodium salt of diisobutylnaphthalene-α-sulfonic acid, 10 parts by weight of the sodium salt of a lignosulfonic acid from a sulfite waste liquor and 7 parts by weight of pulverulent silica gel, and ground in a hammer mill (active compound content 80% by weight).

PREPARATION EXAMPLES

Example 1

α-L-Arabino-3-hexulofuranosonic acid, 2-C-[2-nitro-1-phenylethyl], γ-lactone (compound Ib.007, Table 11)

With stirring, 1.4 g (10 mmol) of nitrostyrene were added to 3.5 g (20 mmol) of D-isoascorbic acid in 50 ml of a 50% strength solution of ethanol, and the mixture was stirred at 23° C. for 5 days, with DC monitoring. The reaction solution was concentrated under reduced pressure, taken up in 100 ml of diethyl ether and extracted with water. After drying over sodium sulfate and concentration under reduced pressure, this gave 2.3 g (71% of theory) of the title compound as a foam-like yellow solid. IR (KBr, ν [cm$^{-1}$]: 3440 (OH), 2924 (CH), 1782 lactone, 1554 (NO$_2$).

Example 2

α-L-Xylo-3-hexulofuranosonic acid, 2-C-(2-bromo-2-nitro-1-phenylethyl), γ-lactone (compound Ia.034 of Table 9)

With stirring, 1.7 g (10 mmol) of L-ascorbic acid were added to a mixture of 1.1 g (5 mmol) of β-bromonitrostyrene in 40 ml of ethanol and 10 ml of water, and the mixture was stirred at 27–30° C. for 4 days, with DC monitoring. The reaction solution was concentrated under reduced pressure, taken up in 100 ml of ethyl acetate and extracted with water. After drying over magnesium sulfate and concentration under reduced pressure, this gave 0.85 g (49% of theory) of the title compound as a foam-like yellow solid. IR (KBr, ν [cm$^{-1}$]): 3426 (OH); 2924 (CH); 1774 (lactone); 1576 (NO$_2$).

Example 3

2,5-Di-O-(2',4'-hexadienyloxy)-α-L-xylo-3-hexulofuranosonic acid, 2—C-(2'-nitro-1'-[4'-chlorophenyl]ethyl), γ-lactone (compound Ia.064 of Table 10)

Over a period of 5 min, 1.15 g [5.56 mmol] of dicyclohexylcarbodiimide were added with stirring to a suspension of 1 g [2.78 mmol] of the compound Ia.008, Table 9, 0.62 g [5.56 mmol] of sorbic acid and 50 mg of 4-[1-pyrrolidinyl]pyridine in 100 ml of methylene chloride. After 18 h of stirring at 22° C., the resulting urea was filtered off with suction and the filtrate was washed 2 times using 1N hydrochloric acid. The organic phase was washed with water and saturated sodium chloride solution, dried and concentrated. Purification by silica gel chromatography using toluene/ethyl acetate 9:1 gave 0.91 g (59% of theory) of the title compound as a foam-like colorless solid. IR (KBr, ν [cm$^{-1}$]: 3432 (OH), 2855 (CH), 1805 (lactone), 1714, 1642 [C═O]).

Using appropriately modified starting compounds, the procedures described in the synthetic examples above were used to obtain further nitroethane derivatives of the formulae Ia and Ib. Selected physical data of the nitroethane derivatives Ia are listed in Tables 9 and 10 below, and those of the nitroethane derivatives Ib are listed in Table 11.

TABLE 9

Compounds Ia where R$^2$ = H

| No. | R$^1$ | A | IR (KBr, ν [cm$^{-1}$], mp (° C.), 1H NMR (δ [ppm]) |
|---|---|---|---|
| Ia.001 | H | 4-fluorophenyl | 3454 (OH), 2926 (CH), 1790 (lactone), 1556 (NO$_2$) |
| Ia.002 | H | 3-fluorophenyl | |
| Ia.003 | H | 2-fluorophenyl | |
| Ia.004 | H | 4-nitrophenyl | 3454 (OH), 2926 (CH), 1790 (lactone), 1556 (NO$_2$) |
| Ia.005 | H | 3-nitrophenyl | 3450 (OH), 2978 (CH), 1790 (lactone), 1556, 1532 (NO$_2$) |
| Ia.006 | H | 2-nitrophenyl | |
| Ia.007 | H | phenyl | 64–66* |
| Ia.008 | H | 4-chlorophenyl | 65–72* |
| Ia.009 | H | 3-chlorophenyl | |
| Ia.010 | H | 2-chlorophenyl | |
| Ia.011 | H | 2,4-dichlorophenyl | |
| Ia.012 | H | 2,3-dichlorophenyl | |

TABLE 9-continued

Compounds Ia where R$^2$ = H

| No. | R$^1$ | A | IR (KBr, ν [cm$^{-1}$], mp (° C.), 1H NMR (δ [ppm]) |
|---|---|---|---|
| Ia.013 | H | 2,6-dichlorophenyl | 1791 (lactone), 1556, 1380 (NO$_2$), 1033 ar-Cl* |
| Ia.014 | H | 4-methylphenyl | 2.27 (s, CH$_3$), 7.16 (d, phenyl-H)* |
| Ia.015 | H | 3-methylphenyl | |
| Ia.016 | H | 2-methylphenyl | |
| Ia.017 | H | 2-chloro-4-methylphenyl | |
| Ia.018 | H | 4-chloro-2-methylphenyl | |
| Ia.019 | H | 4-methoxyphenyl | 65–70* |
| Ia.020 | H | 3-methoxyphenyl | 65–70* |
| Ia.021 | H | 2-methoxyphenyl | 80–85* |
| Ia.022 | H | 3-chloro-2-methoxyphenyl | |
| Ia.023 | H | 3,5-dichloro-2-methoxyphenyl | |
| Ia.024 | H | 3-chloro-4-methoxyphenyl | |
| Ia.025 | H | 3-hydroxy-4-methoxyphenyl | 74* |
| Ia.026 | H | 3-chloro-4-methylphenyl | |
| Ia.027 | H | 3,4,5-trimethoxyphenyl | 3406 (OH), 2972, 2946, 2448 (CH), 1786 (lactone), 1544 (NO$_2$) |
| Ia.028 | Br | 4-fluorophenyl | |
| Ia.029 | Br | 3-fluorophenyl | |
| Ia.030 | Br | 2-fluorophenyl | |
| Ia.031 | Br | 4-nitrophenyl | |
| Ia.032 | Br | 3-nitrophenyl | |
| Ia.033 | Br | 2-nitrophenyl | |
| Ia.034 | Br | phenyl | 3426 (OH), 2924 (CH), 1774 (lactone), 1576 (NO$_2$) |
| Ia.035 | Br | 4-chlorophenyl | 3500 (OH), 2962 (CH); 1792 (lactone), 1572 (NO$_2$) |
| Ia.036 | Br | 3-chlorophenyl | |
| Ia.037 | Br | 2-chlorophenyl | |
| Ia.038 | Br | 2,4-dichlorophenyl | |
| Ia.039 | Br | 2,3-dichlorophenyl | |
| Ia.040 | Br | 2,6-dichlorophenyl | |
| Ia.041 | Br | 4-methylphenyl | |
| Ia.042 | Br | 3-methylphenyl | |
| Ia.043 | Br | 2-methylphenyl | |
| Ia.044 | Br | 2-chloro-4-methylphenyl | |
| Ia.045 | Br | 4-chloro-2-methylphenyl | |
| Ia.046 | Br | 4-methoxyphenyl | |
| Ia.047 | Br | 3-methoxyphenyl | |
| Ia.048 | Br | 2-methoxyphenyl | |
| Ia.049 | Br | 3-chloro-2-methoxyphenyl | |
| Ia.050 | Br | 3,5-dichloro-2-methoxyphenyl | |
| Ia.051 | Br | 3-chloro-4-methoxyphenyl | |
| Ia.052 | Br | 3-hydroxy-4-methoxyphenyl | |
| Ia.053 | Br | 3-chloro-4-methylphenyl | |
| Ia.054 | Cl | 4-fluorophenyl | |
| Ia.055 | Cl | 4-chlorophenyl | |
| Ia.056 | Cl | 4-methylphenyl | |
| Ia.057 | Cl | 4-methyl-3-chlorophenyl | |
| Ia.058 | Cl | 4-methoxyphenyl | |
| Ia.059 | Cl | 4-nitrophenyl | |

*Pharmazie 51 (1996) 1, 11–16

TABLE 10

Compounds Ia where $R^2 \neq H$

Ia

| No. | $R^1$ | $R^2$ | A | IR (KBr, ν [cm$^{-1}$], mp (° C.), 1H NMR (δ [ppm]) |
|---|---|---|---|---|
| Ia.060 | H | HC[O] | 4-fluorophenyl | |
| Ia.061 | Br | CH$_3$C[O] | 4-fluorophenyl | |
| Ia.062 | H | HC[O] | 4-chlorophenyl | |
| Ia.063 | H | CH$_3$C[O] | 4-chlorophenyl | |
| Ia.064 | H | 2,4-hexa-dienoyl | 4-chlorophenyl | 3432 (OH), 2855 (CH), 1805 (lactone), 1714, 1642 [C=O] |
| Ia.065 | H | CH$_3$C[O] | 3-chlorophenyl | |
| Ia.066 | Br | CH$_3$C[O] | 4-chlorophenyl | |
| Ia.067 | H | CH$_3$C[O] | 4-nitrophenyl | |
| Ia.068 | H | C$_2$H$_5$C[O] | 2,4-dichloro-phenyl | |
| Ia.069 | Br | CH$_3$C[O] | 3,4-dichloro-phenyl | |
| Ia.070 | H | CH$_3$C[O] | 4-methylphenyl | |
| Ia.071 | Br | CH$_3$C[O] | 4-methoxyphenyl | |
| Ia.072 | H | CH$_3$C[O] | 3-chloro-4-methoxyphenyl | |
| Ia.073 | H | C$_3$H$_7$C[O] | 4-chlorophenyl | |
| Ia.074 | Br | nC$_4$H$_9$C[O] | 4-nitrophenyl | |
| Ia.075 | H | CH$_3$C[O] | 3-chloro-4-methylphenyl | |
| Ia.076 | H | C$_2$H$_5$C[O] | 3-chlorophenyl | |
| Ia.077 | Br | CH$_3$C[O] | 3-chlorophenyl | |
| Ia.078 | Br | nC$_3$H$_7$C[O] | 3-chlorophenyl | |
| Ia.079 | H | HC[O] | 3-nitrophenyl | |
| Ia.080 | H | CH$_3$C[O] | 3-nitrophenyl | |
| Ia.081 | Br | CH$_3$C[O] | 3-nitrophenyl | |

TABLE 11

Compounds Ib where $R^2 = H$

| No. | $R^1$ | A | IR (KBr, ν [cm$^{-1}$], mp (° C.), 1H NMR (δ [ppm]) |
|---|---|---|---|
| Ib.001 | H | 4-fluorophenyl | |
| Ib.002 | H | 3-fluorophenyl | |
| Ib.003 | H | 2-fluorophenyl | |
| Ib.004 | H | 4-nitrophenyl | |
| Ib.005 | H | 3-nitrophenyl | |
| Ib.006 | H | 2-nitrophenyl | |
| Ib.007 | H | phenyl | 3440 (OH), 2924 (CH), 1782 (lactone), 1554 (NO$_2$) |
| Ib.008 | H | 4-chlorophenyl | |
| Ib.009 | H | 3-chlorophenyl | |
| Ib.010 | H | 2-chlorophenyl | |
| Ib.011 | H | 2,4-dichlorophenyl | |
| Ib.012 | H | 2,3-dichlorophenyl | |
| Ib.013 | H | 2,6-dichlorophenyl | |
| Ib.014 | H | 4-methylphenyl | |
| Ib.015 | H | 3-methylphenyl | |
| Ib.016 | H | 2-methylphenyl | |
| Ib.017 | H | 2-chloro-4-methylphenyl | |
| Ib.018 | H | 4-chloro-2-methylphenyl | |
| Ib.019 | H | 4-methoxyphenyl | 3442 (OH), 2966 (CH), 1786 (lactone), 1554 (NO$_2$) |
| Ib.020 | H | 3-methoxyphenyl | |
| Ib.021 | H | 2-methoxyphenyl | |
| Ib.022 | H | 3-chloro-2-methoxyphenyl | |
| Ib.023 | H | 3,5-dichloro-2-methoxy-phenyl | |
| Ib.024 | H | 3-chloro-4-methoxyphenyl | |
| Ib.025 | H | 3-hydroxy-4-methoxyphenyl | |
| Ib.026 | H | 3-chloro-4-methylphenyl | |
| Ib.027 | H | 3,4,5-trimethoxyphenyl | 3406 (OH), 2946, 2848 (CH), 1786 (lactone), 1544 (NO$_2$) |
| Ib.028 | Br | 4-fluorophenyl | |
| Ib.029 | Br | 3-fluorophenyl | |
| Ib.030 | Br | 2-fluorophenyl | |
| Ib.031 | Br | 4-nitrophenyl | |
| Ib.032 | Br | 3-nitrophenyl | |
| Ib.033 | Br | 2-nitrophenyl | |
| Ib.034 | Br | phenyl | |
| Ib.035 | Br | 4-chlorophenyl | |
| Ib.036 | Br | 3-chlorophenyl | |
| Ib.037 | Br | 2-chlorophenyl | |
| Ib.038 | Br | 2,4-dichlorophenyl | |
| Ib.039 | Br | 2,3-dichlorophenyl | |
| Ib.040 | Br | 2,6-dichlorophenyl | |
| Ib.041 | Br | 4-methylphenyl | |
| Ib.042 | Br | 3-methylphenyl | |
| Ib.043 | Br | 2-methylphenyl | |
| Ib.044 | Br | 2-chloro-4-methylphenyl | |
| Ib.045 | Br | 4-chloro-2-methylphenyl | |
| Ib.046 | Br | 4-methoxyphenyl | |
| Ib.047 | Br | 3-methoxyphenyl | |
| Ib.048 | Br | 2-methoxyphenyl | |
| Ib.049 | Br | 3-chloro-2-methoxyphenyl | |
| Ib.050 | Br | 3,5-dichloro-2-methoxy-phenyl | |
| Ib.051 | Br | 3-chloro-4-methoxyphenyl | |
| Ib.052 | Br | 3-hydroxy-4-methoxyphenyl | |
| Ib.053 | Br | 3-chloro-4-methylphenyl | |
| Ib.054 | Cl | 4-fluorophenyl | |
| Ib.055 | Cl | 4-chlorophenyl | |
| Ib.056 | Cl | 4-methylphenyl | |
| Ib.057 | Cl | 4-methyl-3-chlorophenyl | |
| Ib.058 | Cl | 4-methoxyphenyl | |
| Ib.059 | Cl | 4-nitrophenyl | |

We claim:

1. A method for protecting industrial materials against attack and destruction by microorganisms, which comprises treating the industrial materials with a microbicidally effective amount of a nitroethane compound of formula I

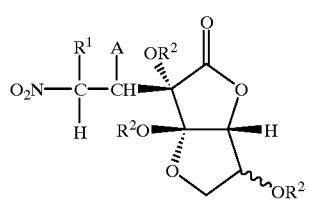

I wherein $R^1$ is hydrogen, $C_1$–$C_6$-alkyl which may be substituted by halogen, cyano, hydroxycarbonyl, $C_1$–$C_3$-alkoxy, $C_1$–$C_3$-alkylthio, $C_1$–$C_3$-alkoxycarbonyl, or is $C_3$–$C_6$-alkenyl, $C_3$–$C_6$-alkynyl, halogen, cyano or thiocyanato;

$R^2$ is hydrogen, formyl; halogen- or $C_1$–$C_3$-alkoxy-substituted or unsubstituted $C_1$–$C_6$-alkylcarbonyl, $C_2$–$C_6$-alkenylcarbonyl, $C_4$–$C_6$-alkyldienylcarbonyl or $C_2$–$C_6$-alkynylcarbonyl;

A is phenyl, naphthyl, quinolyl, quinazolyl, quinoxalyl, 1-methylindolyl, 1-methylbenzimidazolyl, 2-methylindazolyl, benzofuranyl, benzothienyl, benzoxazolyl, benzothiazolyl, which may carry a divalent substituent such as methylenedioxy, difluoromethylenedioxy, chlorofluoromethylenedioxy, dichloromethylenedioxy in adjacent positions or may in each case be mono- to pentasubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, amino, $C_1$–$C_4$-monoalkylamino, $C_1$–$C_4$-dialkylamino, $C_3$–$C_6$-cycloalkyl, $C_1$–$C_4$-alkoxycarbonyl, $C_1$–$C_4$-alkoxycarbonyl-$C_1$–$C_4$-alkyl, hydroxyl, nitro or cyano; is furyl, thienyl, pyrrolyl, isoxazolyl, isothiazolyl, pyrazolyl, oxazolyl, thiazolyl, imidazolyl, oxadiazolyl, thiadiazolyl, triazolyl, pyridinyl, pyridazinyl, pyrimidinyl, pyrazinyl or triazinyl, pyranyl or thiopyranyl which may in each case be mono- to trisubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, amino, $C_1$–$C_4$-monoalkylamino, $C_1$–$C_4$-dialkylamino, $C_3$–$C_6$-cycloalkyl, $C_1$–$C_4$-alkoxycarbonyl, $C_1$–$C_4$-alkoxycarbonyl-$C_1$–$C_4$-alkyl, hydroxyl, nitro or cyano; as microbicides.

2. The method of claim 1 wherein
$R^1$ is hydrogen, $C_1$–$C_4$-alkyl which may be substituted by halogen, cyano, hydroxycarbonyl, $C_1$–$C_3$-alkoxy, $C_1$–$C_3$-alkylthio, $C_1$–$C_3$-alkoxycarbonyl, or is halogen;
$R^2$ is hydrogen.

3. The method of claim 1 wherein
$R^1$ is hydrogen or halogen;
$R^2$ is hydrogen;
A is phenyl, naphthyl, quinolyl, quinazolyl, quinoxalyl, benzofuranyl, benzothienyl, benzoxazolyl, benzothiazolyl, which may carry a divalent substituent such as methylenedioxy, difluoromethylenedioxy, chlorofluoromethylenedioxy in adjacent positions or may in each case be mono- to trisubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkoxycarbonyl, hydroxyl, nitro or cyano; is furanyl, thienyl, pyrrolyl, isoxazolyl, isothiazolyl, pyrazolyl, oxazolyl, thiazolyl, imidazolyl, oxadiazolyl, pyridyl, pyranyl or thiopyranyl, each of which may be mono- to disubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkoxycarbonyl, nitro or cyano.

4. A nitroethane compound of formula Ia

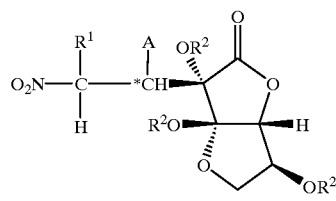

Ia wherein A and $R^2$ are each as defined in claim 1 and
$R^1$ is $C_1$–$C_6$-alkyl which may be substituted by halogen, cyano, hydroxycarbonyl, $C_1$–$C_3$-alkoxy, $C_1$–$C_3$-alkylthio, $C_1$–$C_3$-alkoxycarbonyl, or is $C_3$–$C_6$-alkenyl, $C_3$–$C_6$-alkynyl, halogen, cyano or thiocyanato.

5. The nitroethane compound of formula Ia defined in claim 4 wherein
A is phenyl, naphthyl, quinolyl, quinazolyl, quinoxalyl, 1-methylindolyl, 1-methylbenzimidazolyl, 2-methylindazolyl, benzofuranyl, benzothienyl, benzoxazolyl, benzothiazolyl, which may carry a divalent substituent such as methylenedioxy, difluoromethylenedioxy, chlorofluoromethylenedioxy, dichloromethylenedioxy in adjacent positions or may in each case be mono- to pentasubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, amino, $C_1$–$C_4$-monoalkylamino, $C_1$–$C_4$-dialkylamino, $C_3$–$C_6$-cycloalkyl, $C_1$–$C_4$-alkoxycarbonyl, $C_1$–$C_4$-alkoxycarbonyl-$C_1$–$C_4$-alkyl, hydroxyl, nitro or cyano; is furyl, thienyl, pyrrolyl, isoxazolyl, isothiazolyl, pyrazolyl, oxazolyl, thiazolyl, imidazolyl, oxadiazolyl, thiadiazolyl, triazolyl, pyridinyl, pyridazinyl, pyrimidinyl, pyrazinyl or triazinyl, pyranyl or thiopyranyl which may in each case be mono- to trisubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, amino, $C_1$–$C_4$-monoalkylamino, $C_1$–$C_4$-dialkylamino, $C_3$–$C_6$-cycloalkyl, $C_1$–$C_4$-alkoxycarbonyl, $C_1$–$C_4$-alkoxycarbonyl-$C_1$–$C_4$-alkyl, hydroxyl, nitro or cyano;
$R^1$ is hydrogen and
$R^2$ is formyl; halogen- or $C_1$–$C_3$-alkoxy-substituted or unsubstituted $C_1$–$C_6$-alkylcarbonyl, $C_2$–$C_6$-alkenylcarbonyl, $C_4$–$C_6$-alkyldienylcarbonyl or $C_2$–$C_6$-alkynylcarbonyl.

6. The nitroethane compound of formula Ia defined in claim 4 wherein
$R^2$ is hydrogen;
A is phenyl, naphthyl, quinolyl, quinazolyl, quinoxalyl, benzofuranyl, benzothienyl, benzoxazolyl, benzothiazolyl, which may carry a divalent substituent such as methylenedioxy, difluoromethylenedioxy, chlorofluoromethylenedioxy in adjacent positions or may in each case be mono- to trisubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkoxycarbonyl, hydroxyl, nitro or cyano; is furanyl, thienyl, pyrrolyl, isoxazolyl, isothiazolyl, pyrazolyl, oxazolyl, thiazolyl, imidazolyl, oxadiazolyl, pyridyl, pyranyl or thiopyranyl, each of which may be mono- to disubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkoxycarbonyl, nitro or cyano, and
$R^1$ is halogen.

7. A process for preparing the nitroethane compound of formula Ia defined in claim 4 or of formula Ib

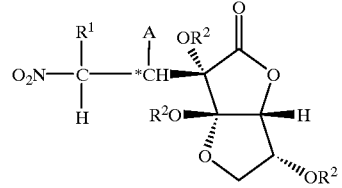

Ib wherein A, $R^1$ and $R^2$ are as defined for formula Ia, which comprises reacting a nitrostyrene of formula II

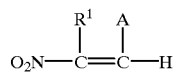

in which $R^1$ and A are each $R^1$ is $C_1$–$C_6$-alkyl which may be substituted by halogen, cyano, hydroxycarbonyl, $C_1$–$C_3$-alkoxy, $C_1$–$C_3$-alkylthio, $C_1$–$C_3$-alkoxycarbonyl, or is $C_3$–$C_6$-alkenyl, $C_3$–$C_6$-alkynyl, halogen, cyano or thiocyanato;

A is phenyl, naphthyl, quinolyl, quinazolyl, quinoxalyl, 1-methylindolyl, 1-methylbenzimidazolyl, 2-methylindazolyl, benzofuranyl, benzothienyl, benzoxazolyl, benzothiazolyl, which may carry a divalent substituent such as methylenedioxy, difluoromethylenedioxy, chlorofluoromethylenedioxy, dichloromethylenedioxy in adjacent positions or may in each case mono- to pentasubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, amino, $C_1$–$C_4$-monoalkylamino, $C_1$–$C_4$-dialkylamino, $C_3$–$C_6$-cycloalkyl, $C_1$–$C_4$-alkoxycarbonyl, $C_1$–$C_4$-alkoxycarbonyl-$C_1$–$C_4$-alkyl, hydroxyl, nitro or cyano; is furyl, thienyl, pyrrolyl, isoxazolyl, isothiazolyl, pyrazolyl, oxazolyl, thiazolyl, imidazolyl, oxadiazolyl, thiadiazolyl, triazolyl, pyridinyl, pyridazinyl, pyrimidinyl, pyrazinyl or triazinyl, pyranyl or thiopyranyl which may in each case be mono- to trisubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, amino, $C_1$–$C_4$-monoalkylamino, $C_1$–$C_4$-dialkylamino, $C_3$–$C_6$-cycloalkyl, $C_1$–$C_4$-alkoxycarbonyl, $C_1$–$C_4$-alkoxycarbonyl-$C_1$–$C_4$-alkyl, hydroxyl, nitro or cyano;

with L-ascorbic acid of formula IIIa

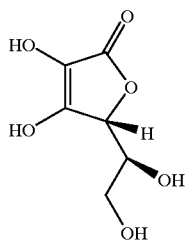

or with D-isoascorbic acid of formula IIIb

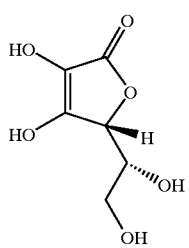

and, if appropriate, treating the resulting nitroethane derivatives of the formula I in which $R^2$ is hydrogen with an acylating agent, thus giving nitroethane derivatives of the formula I in which at least some $R^2$ radicals are not hydrogen.

8. A composition, comprising a microbicidally effective amount of at least one nitroethane compound of formula Ia as defined in claim 4 and at least one inert liquid and/or solid carrier and optionally at least one surfactant.

9. The composition defined in claim 8, wherein

A is phenyl, naphthyl, quinolyl, quinazolyl, quinoxalyl, 1-methylindolyl, 1-methylbenzimidazolyl, 2-methylindazolyl, benzofuranyl, benzothienyl, benzoxazolyl, benzothiazolyl, which may carry a divalent substituent such as methylenedioxy, difluoromethylenedioxy, chlorofluoromethylenedioxy, dichloromethylenedioxy in adjacent positions or may in each case be mono- to pentasubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, amino, $C_1$–$C_4$-monoalkylamino, $C_1$–$C_4$-dialkylamino, $C_3$–$C_6$-cycloalkyl, $C_1$–$C_4$-alkoxycarbonyl, $C_1$–$C_4$-alkoxycarbonyl-$C_1$–$C_4$-alkyl, hydroxyl, nitro or cyano; is furyl, thienyl, pyrrolyl, isoxazolyl, isothiazolyl, pyrazolyl, oxazolyl, thiazolyl, imidazolyl, oxadiazolyl, thiadiazolyl, triazolyl, pyridinyl, pyridazinyl, pyrimidinyl, pyrazinyl or triazinyl, pyranyl or thiopyranyl which may in each case be mono- to trisubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, amino, $C_1$–$C_4$-monoalkylamino, $C_1$–$C_4$-dialkylamino, $C_3$–$C_6$-cycloalkyl, $C_1$–$C_4$-alkoxycarbonyl, $C_1$–$C_4$-alkoxycarbonyl-$C_1$–$C_4$-alkyl, hydroxyl, nitro or cyano;

$R^1$ is hydrogen and $R^2$ is formyl; halogen- or $C_1$–$C_3$-alkoxy-substituted or unsubstituted $C_1$–$C_6$-alkylcarbonyl, $C_2$–$C_6$-alkenylcarbonyl, $C_4$–$C_6$-alkyldienylcarbonyl or $C_2$–$C_6$-alkynylcarbonyl.

10. The composition defined in claim 8, wherein $R^2$ is hydrogen;

A is phenyl, naphthyl, quinolyl, quinazolyl, quinoxalyl, benzofuranyl, benzothienyl, benzoxazolyl, benzothiazolyl, which may carry a divalent substituent such as methylenedioxy, difluoromethylenedioxy, chlorofluoromethylenedioxy in adjacent positions or may in each case be mono- to trisubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkoxycarbonyl, hydroxyl, nitro or cyano;

is furanyl, thienyl, pyrrolyl, isoxazolyl, isothiazolyl, pyrazolyl, oxazolyl, thiazolyl, imidazolyl, oxadiazolyl, pyridyl, pyranyl or thiopyranyl, each of which may be mono- to disubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkoxycarbonyl, nitro or cyano, and $R^1$ is halogen.

11. A nitroethane compound of formula Ib

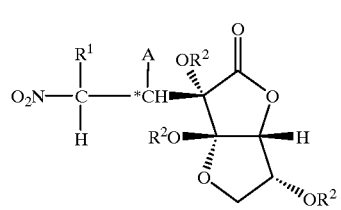

wherein A and $R^2$ are each as defined in claim 1 and $R^1$ is $C_1$–$C_6$-alkyl which may be substituted by halogen, cyano, hydroxycarbonyl, $C_1$–$C_3$-alkoxy, $C_1$–$C_3$- alkylthio, $C_1$–$C_3$-alkoxycarbonyl, or is $C_3$–$C_6$-alkenyl, $C_3$–$C_6$-alkynyl, halogen, cyano or thiocyanato.

12. The nitroethane compound of formula Ib defined in claim 11 wherein

A is phenyl, naphthyl, quinolyl, quinazolyl, quinoxalyl, 1-methylindolyl, 1-methylbenzimidazolyl, 2-methylindazolyl, benzofuranyl, benzothienyl, benzoxazolyl, benzothiazolyl, which may carry a divalent substituent such as methylenedioxy, difluoromethylenedioxy, chlorofluoromethylenedioxy, dichloromethylenedioxy in adjacent positions or may in each case be mono- to pentasubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, amino, $C_1$–$C_4$-monoalkylamino, $C_1$–$C_4$-dialkylamino, $C_3$–$C_6$-cycloalkyl, $C_1$–$C_4$-alkoxycarbonyl, $C_1$–$C_4$-alkoxycarbonyl-$C_1$–$C_4$-alkyl, hydroxyl, nitro or cyano; is furyl, thienyl, pyrrolyl, isoxazolyl, isothiazolyl, pyrazolyl, oxazolyl, thiazolyl, imidazolyl, oxadiazolyl, thiadiazolyl, triazolyl, pyridinyl, pyridazinyl, pyrimidinyl, pyrazinyl or triazinyl, pyranyl or thiopyranyl which may in each case be mono- to trisubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, amino, $C_1$–$C_4$-monoalkylamino, $C_1$–$C_4$-dialkylamino, $C_3$–$C_6$-cycloalkyl, $C_1$–$C_4$-alkoxycarbonyl, $C_1$–$C_4$-alkoxycarbonyl-$C_1$–$C_4$-alkyl, hydroxyl, nitro or cyano;

$R^1$ is hydrogen and $R^2$ is formyl; halogen- or $C_1$–$C_3$-alkoxy-substituted or unsubstituted $C_1$–$C_6$-alkylcarbonyl, $C_2$–$C_6$-alkenylcarbonyl, $C_4$–$C_6$-alkyldienylcarbonyl or $C_2$–$C_6$-alkynylcarbonyl.

13. The nitroethane compound of formula Ib defined in claim 11 wherein $R^2$ is hydrogen;

A is phenyl, naphthyl, quinolyl, quinazolyl, quinoxalyl, benzofuranyl, benzothienyl, benzoxazolyl, benzothiazolyl, which may carry a divalent substituent such as methylenedioxy, difluoromethylenedioxy, chlorofluoromethylenedioxy in adjacent positions or may in each case be mono- to trisubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkoxycarbonyl, hydroxyl, nitro or cyano; is furanyl, thienyl, pyrrolyl, isoxazolyl, isothiazolyl, pyrazolyl, oxazolyl, thiazolyl, imidazolyl, oxadiazolyl, pyridyl, pyranyl or thiopyranyl, each of which may be mono- to disubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkoxycarbonyl, nitro or cyano, and $R^1$ is halogen.

14. A composition, comprising a microbicidally effective amount of at least one nitroethane compound of formula Ib as defined in claim 11 and at least one inert liquid and/or solid carrier andoptionally at least one surfactant.

15. The composition defined in claim 14, wherein

A is phenyl, naphthyl, quinolyl, quinazolyl, quinoxalyl, 1-methylindolyl, 1-methylbenzimidazolyl, 2-methylindazolyl, benzofuranyl, benzothienyl, benzoxazolyl, benzothiazolyl, which may carry a divalent substituent such as methylenedioxy, difluoromethylenedioxy, chlorofluoromethylenedioxy, dichloromethylenedioxy in adjacent positions or may in each case be mono- to pentasubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, amino, $C_1$–$C_4$-monoalkylamino, $C_1$–$C_4$-dialkylamino, $C_3$–$C_6$-cycloalkyl, $C_1$–$C_4$-alkoxycarbonyl, $C_1$–$C_4$-alkoxycarbonyl-$C_1$–$C_4$-alkyl, hydroxyl, nitro or cyano; is furyl, thienyl, pyrrolyl, isoxazolyl, isothiazolyl, pyrazolyl, oxazolyl, thiazolyl, imidazolyl, oxadiazolyl, thiadiazolyl, triazolyl, pyridinyl, pyridazinyl, pyrimidinyl, pyrazinyl or triazinyl, pyranyl or thiopyranyl which may in each case be mono- to trisubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, amino, $C_1$–$C_4$-monoalkylamino, $C_1$–$C_4$-dialkylamino, $C_3$–$C_6$-cycloalkyl, $C_1$–$C_4$-alkoxycarbonyl, $C_1$–$C_4$-alkoxycarbonyl-$C_1$–$C_4$-alkyl, hydroxyl, nitro or cyano;

$R^1$ is hydrogen and $R^2$ is formyl; halogen- or $C_1$–$C_3$-alkoxy-substituted or unsubstituted $C_1$–$C_6$-alkylcarbonyl, $C_2$–$C_6$-alkenylcarbonyl, $C_4$–$C_6$-alkyldienylcarbonyl or $C_2$–$C_6$-alkynylcarbonyl.

16. The composition defined in claim 14, wherein $R^2$ is hydrogen;

A is phenyl, naphthyl, quinolyl, quinazolyl, quinoxalyl, benzofuranyl, benzothienyl, benzoxazolyl, benzothiazolyl, which may carry a divalent substituent such as methylenedioxy, difluoromethylenedioxy, chlorofluoromethylenedioxy in adjacent positions or may in each case be mono- to trisubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkoxycarbonyl, hydroxyl, nitro or cyano; is furanyl, thienyl, pyrrolyl, isoxazolyl, isothiazolyl, pyrazolyl, oxazolyl, thiazolyl, imidazolyl, oxadiazolyl, pyridyl, pyranyl or thiopyranyl, each of which may be mono- to disubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkoxycarbonyl, nitro or cyano, and $R^1$ is halogen.

* * * * *

UNITED STATES PATENT AND TRADEMARK OFFICE
CERTIFICATE OF CORRECTION

PATENT NO. : 6,268,514 B1
DATED : July 31, 2001
INVENTOR(S) : Hamprecht et al.

It is certified that error appears in the above-identified patent and that said Letters Patent is hereby corrected as shown below:

Column 41, claim 7,
Line 18, "dichlorome thylenedioxy" should be -- dichloromethylenedioxy --.

Column 44, claim 14,
Line 2, "andoptionally" should be -- and optionally --.

Signed and Sealed this

Eleventh Day of December, 2001

Attest:

NICHOLAS P. GODICI
Attesting Officer
Acting Director of the United States Patent and Trademark Office